(12) United States Patent
Kay

(10) Patent No.: US 8,425,921 B1
(45) Date of Patent: Apr. 23, 2013

(54) LIPID RAFT, CAVEOLIN PROTEIN, AND CAVEOLAR FUNCTION MODULATION COMPOUNDS AND ASSOCIATED SYNTHETIC AND THERAPEUTIC METHODS

(76) Inventor: Heidi Kay, Nashville, TN (US)

( * ) Notice: Subject to any disclaimer, the term of this patent is extended or adjusted under 35 U.S.C. 154(b) by 0 days.

(21) Appl. No.: 13/245,279

(22) Filed: Sep. 26, 2011

Related U.S. Application Data

(62) Division of application No. 12/122,855, filed on May 19, 2008, now Pat. No. 8,026, 382.

(60) Provisional application No. 60/938,781, filed on May 18, 2007.

(51) Int. Cl.
*A61K 45/00* (2006.01)
*A61K 31/28* (2006.01)
*C07F 15/00* (2006.01)

(52) U.S. Cl.
USPC .................. 424/278.1; 556/137; 514/492

(58) Field of Classification Search .................. 556/137; 514/492; 424/278.1
See application file for complete search history.

(56) References Cited

U.S. PATENT DOCUMENTS

| | | | |
|---|---|---|---|
| 7,238,372 | B2 | 7/2007 | Turkson et al. |
| 7,566,798 | B2 | 7/2009 | Kay |
| 7,759,510 | B2 | 7/2010 | Kay |
| 7,763,585 | B2 | 7/2010 | Turkson et al. |
| 7,977,381 | B2 | 7/2011 | Kay |
| 7,977,500 | B2 | 7/2011 | Kay |
| 8,026,382 | B2 | 9/2011 | Kay |
| 8,247,445 | B2 | 8/2012 | Kay et al. |
| 2005/0074502 | A1 | 4/2005 | Turkson et al. |
| 2005/0080131 | A1 | 4/2005 | Kay et al. |
| 2005/0288365 | A1 | 12/2005 | Kay et al. |
| 2007/0161613 | A1 | 7/2007 | Kay et al. |
| 2008/0187992 | A1 | 8/2008 | Turkson et al. |
| 2008/0286316 | A1 | 11/2008 | Kay |
| 2009/0214626 | A1 | 8/2009 | Kay et al. |
| 2009/0285884 | A1 | 11/2009 | Kay et al. |
| 2010/0190180 | A1 | 7/2010 | Kay et al. |
| 2010/0310645 | A1 | 12/2010 | Turkson et al. |
| 2010/0316704 | A1 | 12/2010 | Kat et al. |
| 2011/0236471 | A1 | 9/2011 | Kay et al. |

OTHER PUBLICATIONS

Sasanelli et al., Journal of Medicinal Chemistry, vol. 50, No. 15, pp. 3434-3441 (2007).*
Arnesano et al., Journal of Medicinal Chemistry, vol. 52, No. 23, pp. 7847-7855 (2009).*

\* cited by examiner

*Primary Examiner* — Porfirio Nazario Gonzalez
(74) *Attorney, Agent, or Firm* — Allen, Dyer, Doppelt, Milbrath & Gilchrist, P.A.

(57) ABSTRACT

The present invention is directed to the modulation of lipid rafts, caveolin proteins, or caveolar functions and processes by platinum(IV) compounds. Caveolae and/or lipid rafts are associated with cell transcription regulation, membrane and cellular transport, cell membrane receptor function, cellular trafficking, antigen presentation, cell differentiation and activation, cytokine modulation, membrane structure and function, and protein modulation. Caveolae, caveolin proteins and lipid rafts are known therapeutic targets for numerous biological functions. Diseases and disorders currently known to be therapeutically targeted through caveolae and/or lipid rafts include diabetes, cancer, cardiovascular diseases, atherosclerosis, pulmonary fibrosis, multiple sclerosis, viral and prion diseases, neuronal disorders, degenerative muscular dystrophies, and autoimmune disorders.

12 Claims, 2 Drawing Sheets

LIPID RAFT, CAVEOLIN PROTEIN, AND CAVEOLAR FUNCTION MODULATION COMPOUNDS AND ASSOCIATED SYNTHETIC AND THERAPEUTIC METHODS

CROSS-REFERENCE TO RELATED APPLICATION

This application claims priority to U.S. patent application Ser. No. 12/122,855 filed May 19, 2008, which claims priority to provisional application Ser. No. 60/938,781, filed on May 18, 2007, contents of which are incorporated herein by reference in their entirety.

BACKGROUND OF THE INVENTION

Both platinum(II) and platinum(IV) compounds have been recognized to be useful as cancer chemotherapeutics since Rosenberg's (and colleagues') discovery in 1965 (Rosenberg, 1965). Cisplatin, cis-diaminodichloroplatinum(II), FDA-approved in 1978; and carboplatin, cis-diaminocyclobutane-1,1-dicarboxylic acid platinum(II), FDA-approved in 1989, continue to be widely prescribed. Both of these platinum(II) compounds form DNA-adducts, primarily responsible for their anticancer properties. Dose-limiting side effects include nephrotoxicity, ototoxicity, gastrointestinal toxicity, neurotoxicity and bone marrow damage; carboplatin exhibits comparatively reduced toxicities, while transplatin (the trans-diaminodichloroplatinum(II) isomer) has been demonstrated to be relatively ineffective for cancer (Kelland, 1994; Singh, 1988). Cisplatin and its analogues have been useful in treatments of testicular, prostate, ovarian, bladder, head and neck, cervical, lung, stomach, and pancreatic cancers. While some undesired effects are reversible, myelosuppression (leukopenia and thrombocytopenia) as well as inherent and acquired resistances are more prohibitive. Newer platinum complexes have been explored, intending to circumvent resistance and reduce toxicities (Kelland, 1999). The approach has largely been towards Pt(IV) prodrugs, reducing to their active Pt(II) analogues through biological reductants, then forming DNA adducts (Hall, 2004); platinum-DNA adducts consistently account for these antitumor activities. Since toxicities have partly been associated with Pt(II)-protein and -sulfur conjugates (Townsend, 2002), Pt(IV) prodrugs can serve to limit these by minimizing serum exposure to the active (+2) form.

Some platinum(IV) complexes, however, have demonstrated unique interactions. Among these are inhibitors of Signal Transducers and Activators of Transcription (STAT) proteins, cytoplasmic transcription factors controlling cellular proliferation, differentiation, development, inflammation, and apoptosis in response to cytokines and growth factors (Turkson, 2004; Kortylewski, 2005). STATs are activated by tyrosine phosphorylation leading to dimerization; dimers translocate to the nucleus, bind to specific DNA response elements, and activate gene expression. Seven STATs have been identified in humans. Of these, STAT3 aberrant activity has been detected in both solid and hematological human tumors (Yu, 2004; Bromberg, 2001; Bromberg, 2002) and describes a new therapeutic target as well as a novel platinum mechanism.

Recently, another novel cellular target has been identified, selective to a subgroup of platinum(IV) complexes. This target is localized within cellular membranes—as opposed to nucleotides or the nucleus—and is composed of caveolae and lipid rafts, identified targets for multiple diseases and key regulators of numerous cellular processes (Tamaskar, 2008; Frank, 2007; Medina, 2007; Silva, 2007; Jasmin, 2006; Medina, 2006; Fine, 2005; Williams, 2005; Williams, 2004; Dhillon, 2003).

Caveolin proteins act either as positive or negative regulators for primary tumor growth, depending upon cell type (Williams, 2005), and thus determine potential therapeutic benefit of platinum(IV) compounds Tumor metastasis, on the other hand, largely relates to reduced caveolin-1 activity together with increased secretions of invasive matrix metalloproteinases-2 and -9 (Williams, 2005) such that therapeutic benefits as a cotherapy for reducing metastasis may be useful for most cancer types. Thus the unique activities in modulating caveolae and lipid rafts for a subset of platinum(IV) compounds identifies specific therapeutic applications for cancers—such as multiple myeloma (Podar, 2006)—different from the indiscriminate DNA-alkylating actions of platinum(II)'s currently in use.

Interactions with caveolae have also been noted for other metals and compounds. Ferrous (Fe(II)), but not ferric (Fe (III)), iron is capable of modulating key cellular signaling proteins by interacting with caveolae (Chen, 2007). Arsenic (III) has also recently been reported to induce increased caveolae/caveolin expressions (Straub, 2007), although the mechanism for this is not clear. Pervanadate and vanadate have both been reported to alter caveolae functions in endothelial cells (Aoki, 2007), while orthovanadate altered caveolin-2 proteins, leading to changes in caveolar activity (Botos, 2007). While no publications appear to identify selenium in caveolae, its activities oppose those of a known caveolae inhibitor, phorbol 12-myristate 13-acetate (Iyengar, 2005), while acting upon proteins known to interface with caveolins (Park, 2007) and thus imply the possibility of another active subgroup of metals affecting caveolae.

Caveolin-1 is one of three known caveolin proteins found in caveolae and in lipid rafts, and is a major decision point in cellular functions. Loss of caveolin-1 function is related not only to certain types of cancer, but to many other human diseases, including those of immune dysfunction, pathogenic infections, diabetes, cardiovascular diseases, and others (Thomas 2008; Cohen 2004; Cohen 2003).

Caveolae, Lipid Rafts, and Caveolins

Lipid rafts are ordered membrane lipid microdomains containing glycosphingolipids and cholesterol. They are characterized (as are caveolae) by their insolubility in cold nonionic detergents. Their involvement in cellular processes is highlighted not only by the co-localization of numerous regulatory proteins, but by the widespread presence of these structures across mammalian cell types. Studies indicate that the plasma membrane is maintained by an active cytoskeleton, whereby the membrane raft hypothesis proposes specific lipids may dynamically associate to form platforms for membrane protein sorting and formation of signaling complexes (Simons, 1997). Their association with membrane receptors involves them in cellular activation and transformation processes, immune synapses (Langlet, 2000), and transport processes.

Caveolae include a number of detergent-insoluble 50-100 nm compositions within a cell membrane, detached vesicles, the Golgi apparatus, endoplasmic reticulum, mitochondria, and other organelles. These may take the form of rafts, tubules, grapes, or vesicular invaginations, composed of sphingolipids, phospholipids, cholesterol, and proteins. The key distinction between caveolae and lipid rafts is the presence of oligomeric caveolin proteins in the former—three, plus their isoforms have been identified—although caveolin proteins also associate in lipid rafts preceding assembly (Hurtado, 2008). Like lipid rafts, caveolae are profoundly involved in human health and diseases (Benarroch, 2007; Michel, 2007; Patra, 2007). In the presence of caveolin proteins, flask or tear-shaped structures are most prevalent, and these tend to be associated with fully differentiated, mature cells. In contrast, the absence of caveolin results primarily in lipid rafts. Caveolae have been associated with most cell types including endothelial and muscle cells, adipocytes, lung epithelial and glial cells, and astrocytes. Of particular significance, they are also present in effector cells of the immune system, including neutrophils, macrophages, mast cells, and dendritic cells (Ohnuma, 2007; Li, 2005; Harris, 2002; Werling, 1997); although some studies identify caveolae-related domains (devoid of caveolin proteins) in hematopoietic cells (Parolini, 1999). Important to vision and retinal diabetes, caveolin proteins and caveolae have been identified in the retina (Berta, 2007). In some cases, caveolin were detected to associate in plasmalemmal and vesicular caveolae (Liu, 2002; Cohen, 2004; Williams, 2004).

The three caveolin proteins (21-24 kD), caveolins-1, -2, and -3, may form homodimers, heterodimers (caveolin 1/2), or larger oligomeric assemblies. Caveolin-1 is the most prevalent of these, being found in most cells, while caveolin-3 had formerly been thought to be restricted to only muscle and heart cells, but is now also recognized to be found in glial cells (Ikezu, 1998; Silva, 2007). Caveolin-2 has been previously described to require caveolin-1 (Parolini, 1999), but its expression and localization within lipid droplets (Fujimoto, 2001) may suggest unique functions; caveolin-2 may also be indicative of basal-like carcinomas (Savage, 2007). Known caveolin functions include lipid and membrane trafficking, membrane structure, and signal transduction. Caveolin-1 is considered fundamental to cholesterol transport (Ikonen, 2004).

Signaling Domain

Caveolae are known to serve as organizational locations for association of intracellular signal transduction proteins (Isshiki, 2002). A growing number of key regulatory proteins have been shown to associate with caveolin-1 through its scaffolding domain (residues 82-101), identified by either sequence *xxxx*xx* or *x*xxxx* (where *=an aromatic residue—tryptophan, phenylalanine or tyrosine and x=any other residue), located in the juxtamembranous region of the N-terminal domain (Couet, 1997). This is part of the "caveolin-1 scaffolding domain hypothesis" (Okamoto, 1998). A partial list of signaling molecules containing this motif and shown to associate with caveolin proteins include: G proteins; Ha-Ras, cNeu and s-Src/Fyn (Src family kinases); endothelial nitric oxide synthase (eNOS), neuronal nitric oxide synthase (nNOS), tyrosine kinase A (TrkA); protein kinase C(PKC); mitogen-activated protein kinase extracellular signal-regulated kinase cascade (MEK/ERK) (Engelman, 1998); protein kinase A (PKA); alkaline phosphatase; phosphofructokinase as well as receptors endothelial growth factor receptor (EGFR); platelet derived growth factor receptor (PDGFR); p75 nerve growth factor receptor (NGFR); estrogen receptor; androgen receptor (Cohen, 2004; Park, 2005); Erb B receptors (Dobrowsky, 2005); transforming growth factor beta receptors (TGFR) types one and two (Santibanez, 2008); vitamin D receptor (Norman, 2006); insulin receptor (Ishikawa, 2005) and others. Caveolins may categorically inhibit kinases (Couet, 1997), since the scaffolding binding motif is contained within a highly conserved subdomain IX of both tyrosine and serine/threonine kinases. Interestingly, the interaction of signaling proteins with caveolin is predominantly a negative regulation, disallowing constitutive activations often associated with cell transformation, viral infection, and cancer.

Trafficking and Transport

Another function of caveolae is endocytotic trafficking. Broadly, there are two mechanisms for endocytosis—those of clathrin-coated pits and those of caveolae. The former mechanism typically includes fusion with lysosomes, where content degradation occurs. The latter appears to bypass lysosomal processes, routing directly to the endoplasmic reticulum (e.g., cholesterol) (Anderson, 1998) or nucleus (i.e., hormones) (Hirata, 2007). Extracellular molecules, ions, and proteins may employ various caveolae-mediated transducers ("transcytosis") to gain functional access to intracellular sites (Ortegren, 2007). This sequence is suspected of transporting microorganisms and infectious components (such as proteins) of viral, parasitic and bacterial diseases and is evidenced by examples of *Escherichia coli* accessing mast cells (Shin, 2001) or Newcastle disease virus infection of host cells (Cantin, 2007), among others. Associations between GPI (glycosylphosphatidylinositol) anchors, extracellular domains, and caveolae may serve as docking sites for cognate receptors facilitating this uptake, while some pathogens may express lipid rafts themselves, participating in infectivity (Campbell, 2004).

Yet another function of caveolae involves assembly and cellular export. Budding processes in the assembly of viral components at lipid raft domains have been observed by several investigators (Nguyen, 2000; Campbell, 2001; Ono, 2001). Limited interactions are known at this time, although coexpression of caveolin-1 with HIV-1 was reported to block viral production (Llano, 2002). HIV Gag protein has also been shown to be targeted to the membrane during assembly and release (Ono, 2004). Prions, amyloid and viral proteins utilize lipid rafts to confer protein conformational changes imperative to their activations (Fantini, 2007).

Caveolae and lipid rafts associate with p-glycoproteins which affect drug uptake into cells. Increased caveolin expression can decrease multi-drug resistance mechanisms, facilitating therapeutic treatments (Storch, 2007; Cai, 2004; Lavie, 2001)

Any of the caveolin-scaffolding proteins can be affected by changes in caveolae. For example, Fyn is a src-family tyrosine kinase. It participates in T-cell receptor signaling and adhesion-mediated signaling, and demonstrates functionalities in fyn (−/−) mice that have myelin defects (Resh, 1998). Decreased caveolin protein functionality would therefore be expected to affect fyn protein activities, for example.

Oncogenesis and Tumor Growth

Caveolin-1 has been associated with cell transformation, oncogenesis, and metastasis, and has been identified as a candidate tumor suppressor (Fiucci, 2002; Wiechen, 2001; Capozza, 2003). Caveolin-1 is often mutated in breast cancer (Lee, 2002), with several isoforms attributed to disease-related dysfunction. Caveolin-1 null mice (Cav-1 (−/−)) showed a 10-fold increase in tumor incidence, a 15-fold increase in tumor number per mouse (multiplicity), and a 35-fold increase in tumor area per mouse, as compared with wild-type littermates following a 16-week exposure to dimethylbenzanthracene (Capozza, 2003). Thus, gene expression of Cav-1 may protect against oncogenesis in certain tumors.

Metastasis

Ras-homology-subfamily GTPases (guanine triphosphate hydrolase enzymes) are involved in actin cytoskeleton rearrangement during cell migration; RhoC GTPase is associated with highly aggressive and metastatic tumors (del Peso, 1997). Along with other Rho-subfamily members, this GTPase contains a caveolin-1 binding domain. In pancreatic adenocarcinomas, caveolin-1 negatively regulates RhoC activation and inhibits cellular migration/invasion associated with metastasis (Lin, 2005).

Many tumors show loss of caveolin-1 expression; when re-expressed, cells lose anchorage-independent mechanisms of growth (Engelman, 1997). Growth of normal cells proceeds through signaling pathways such as Erk (extracellular signal-related kinase), Phosphoinositol kinase (PI3-K), and Rac (a GTPase) that require integrin-mediated cell adhesion, and are therefore, anchorage-dependent. Loss of anchorage-dependent growth is associated with tumor growth and metastasis (Fiucci, 2002). Integrin-mediated cell adhesion binding sites are located within caveolae and transport is facilitated by caveolin-1. In the absence of caveolin-1, GM1 ganglioside remains on cell surfaces where Rac, Erk and Akt (serine-threonine kinase) lose their adhesion-dependence and regulation. Basal GM1 internalization appears to proceed through multiple endocytotic pathways but studies show that internalization induced by detachment is specific to caveolae and caveolin-1 (del Pozo, 2005). These mechanisms demonstrate a role for caveolin-1 in suppression of anchorage-independent growth.

Downregulation of both MMP-2 and MMP-9 (Williams, 2004) have recently been associated with increased presence of Cav-1. These matrix metalloproteinases (MMPs) are also related to loss of anchorage-independent growth, or metastatic potential, as observed in mammary and lung models. MMPs degrade extracellular matrices critical to cell migration, participate in cell proliferation and angiogenesis.

Receptors

The epidermal growth factor receptor (EGFR) is overexpressed in several types of cancer. Under oxidative stress, EGFR is aberrantly phosphorylated by Src kinase and localizes with caveolin-1 to the plasma membrane; later, it transports via caveolar endocytosis to a perinuclear compartment in an active state. This leads to prolonged activation of the receptor and relates to oncogenic potential (Khan, 2006).

EGFR and HER2, ErbB family transmembrane receptor tyrosine kinases, and their ligands are consistently implicated in human (and rodent) breast cancers, including invasive ductal carcinoma of the breast. Additionally, estrogen and progesterone receptors associate with caveolin-1 (Park, 2005). Both receptors are negatively regulated through their interaction with the caveolin-1 scaffolding domain (Okamoto, 1998).

Tumor necrosis factor receptor-1 (TNFR-1) has been shown to be related to caveolae. In cells deficient of lipoproteins, and thus low in membrane cholesterol, reduced cell surface expression of TNFR-1 and CD36 were observed in conjunction with the absence of caveolae. Since TNF-alpha mediates apoptosis, without TNFR-1, this apoptotic pathway can be blocked (Ko, 1999). Thus caveolae mediate cell surface receptors affecting cellular apoptosis.

In adipocytes, insulin reception is directly linked to caveolin-1. Tyrosine phosphorylation is specific for insulin and can be blocked by reducing cholesterol content in the membrane (with beta-methyl-cyclodextrin), essentially eliminating functional caveolae. Metabolic changes, altered free fatty acid and triglyceride levels, and decreased leptin in caveolin-1 null (−/−) mice are similar to prediabetic conditions in humans. Cav-1 null mice also express 90% fewer insulin receptors in adipose tissue (Cohen, 2004). Regulation of caveolin-1 expression is considered an important mechanism for insulin sensitivity (Oh, 2006), while caveolae may have fundamental roles in obesity, diabetes and metabolic disorders (Ortegren, 2007).

Cardiovascular Function

Nitric oxide (NO) is a potent chemokine of the vascular system. Two enzymatic producers of this chemokine, eNos and nNos, contain the scaffolding motif. Reduction of a broad range of inflammatory cytokines through caveolar control such as macrophage inflammatory proteins and monocyte chemoattractant proteins as well as vascular cell adhesion molecule (VCAM-1), cholesterol and fatty acid transport, Interleukin (IL)-6, IL-10, cluster of differentiation (CD)40, and haptoglobin may reduce a broad range of cardiovascular diseases. Caveolin-1-null mice develop cardiac disease similar to hypertrophic cardiomyopathy in humans (Frank, 2004; Cohen, 2003).

Diabetes

Adipocytes are currently known to express the greatest number of caveolae. Given the direct interaction between the insulin receptor and caveolin proteins, as well as effective localization of at least two insulin-responsive elements to caveolae (insulin receptor and GLUT4), a role of caveolae in diabetes as well as metabolic regulation is likely to provide therapeutic utility (Cohen, 2003). Membrane-localized caveolin-1 protein is decreased in diabetic kidneys. Diabetes-mediated alterations in eNOS (endothelial nitric oxide synthase) and caveolin-1 expression are consistent with the view of decreased bioavailability of renal eNOS-derived NO (Komers, 2006). The dissociation of insulin receptor from caveolin-1 is proposed to cause pathogenic signaling in adipocytes (Kabayama, 2007).

Structure

Two mutations in the human CAV-3 gene result in an autosomal-dominant form of limb-girdle muscular dystrophy; mutations on the CAV-3 gene lead to rippling muscle disease (Cohen, 2004). Caveolin-1 is also critical to liver proliferation, lipogenesis, liver regeneration, and lipid metabolism (Frank, 2007; Mayoral, 2007; Fernandez, 2006).

Immunological Response and Antigen Presentation

Cells of the immune system arise from pluripotent stem cells through two main lines of differentiation, the lymphoid lineage and the myeloid lineage. The lymphoid lineage produces lymphocytes, such as T cells, B cells, and natural killer cells, while the myeloid lineage produces monocytes, macrophages, and neutrophils and other accessory cells, such as dendritic cells, platelets, and mast cells. Lymphocytes circulate and search for invading foreign pathogens and antigens that become trapped in secondary lymphoid organs, such as the spleen and lymph nodes.

Antigens are taken up by antigen-presenting cells (APCs). The interaction between T cells and APCs triggers several effector pathways, including activation of cytotoxic T lymphocytes (CTLs) and stimulation of T cell production of cytokines. Major histocompatibility compound (MHC) molecules present antigens on the cell surface of antigen-presenting cells. Cytotoxic T lymphocytes then recognize MHC molecules and their associated peptides and attack the associated target cell. Antigens are processed according to their origin—intracellular or extracellular. Intracellular antigens are presented by class I major histocompatability (MHC) molecules to CD8+ cytotoxic T lymphocytes, effector cells derived from pluripotent stem cells of lymphoid lineage. These are important in resisting pathogens and cancer, and allograft rejection. A distinct route for extracellular antigens use class II MHC molecules, presented to CD4+ helper T cells on the cell surface of APCs such as macrophages.

Caveolae were not originally attributed to cells or lymphatic origin, but this view has changed in the last decade. They have since been identified in human, murine, and bovine neutrophils, macrophages, mast cells, lymphocytes, and antigen-presenting cells (APC) (Harris, 2002; Li, 2005; Ohnuma, 2007). Now, the fundamental role of caveolin proteins and caveolae for immunological response is becoming clearer. For instance, caveolin-1 has been identified to activate thymus cells (T-cells) through the cell surface glycoprotein CD26, leading to activation of nuclear factor kappa beta (NF kappa beta) and T-cell proliferation (Ohnuma, 2007). The mechanism includes upregulation of CD86 expression, a guanylate-kinase-like molecule, CARMA1 and I kappa beta kinase (IKKbeta). CD26, preferentially expressed on the CD4+ memory T-cell subset, binds to caveolin-1 on APCs through the caveolin-scaffolding domain (Ohnuma, 2004). Caveolin-1 has been reported to act as a potent immunomodulatory molecule in macrophages (Wang, 2005). Recent hypotheses also emphasize the critical role of lipid rafts in "immunsynapses" between APCs and T-cells; APCs and B-cells; and B-cells with T-cells (Dustin, 2001; Bromley, 2001). Caveolae and lipid rafts participate in antigen-presentation (Khan, 2007; Sigal 2004; Werling 1999). Hence, these are identified as possible targets of immune-modulation and of immunotherapy (Matko, 2002).

Macrophages are now known to express caveolin-1 (Li, 2005). Loss of caveolin-1 impairs macrophage phagocytosis in Cav-1 knockout mice, suggesting a role in innate immunity, regulation of inflammatory responses and development of autoimmune disease.

Activated Helper T-cells proliferate and secrete a variety of interleukins. However, inadequately-activated T-cells, receiving only one signal in the absence of co-stimulation, become anergized, leading to tolerance (Mueller, 1995).

Murine splenic B-lymphocytes (bone-derived) express caveolin-1. Their activation is dependent upon a Tec family tyrosine kinase known as Bruton's tyrosine kinase (Btk). This kinase has a caveolin-1 scaffolding domain which, when obstructed, prevents B-cell development, differentiation and signaling (Vargas, 2002). Bmx is a human Tec family tyrosine kinase also containing the scaffolding domain.

Two of the most highly expressed Src-family nonreceptor protein tyrosine kinases are $p53/p56^{lyn}$ and $p56^{lck}$. Both are involved in the transduction of signals for proliferation and differentiation of monocytes, B-lymphocytes and T-lymphocytes (thymus-derived), respectively. These have been identified in low-density Triton-insoluble caveolar-like subfractions in leukemic cell lines and granulocytes. Other factors identified in the same subfractions include src (rous sarcoma-like kinase), hck (hemopoietic cell kinase), CD4, CD45, G-proteins, and CD55. These observations lead to the hypothesis for a role of these vesicles in signal transduction mechanisms for hemapoietic cells (Parolini, 1996).

HIV and Other Pathogens

Myristoylation is a signature of caveolar-directed proteins, including Nef protein—present in both HIV and SIV (human and simian immunodeficiency viruses). It is no great surprise to learn that viral proteins seek to hijack cellular signaling, including transduction pathways, associated with caveolar scaffolding. Viruses deficient in functional Nef fail to establish high viral loads or progress into disease. Additionally, Nef protein is sufficient to cause AIDS-like symptoms, and leads to production of inflammatory cytokines which further fuel viral replication and infection (Olivetta, 2003; Hanna, 2006). Downmodulation of both CD4 and MHC1 (major histocompatability-1) result from distinctive endocytotic rerouting in the presence of Nef (Marsh, 2000). Loss of CD4 exposes a cell to reinfection; loss of MHC1 prevents antigen-presentation by the infected cell to the immune system.

Of great significance, Hovanessian et al. (2004) identified a conserved caveolin-1 binding domain in gp41 (glycoprotein-41) of HIV-1, HIV-2, and SIV. Both gp120 and gp41 are viral transmembrane envelope glycoproteins that interact with CD4 and a chemokine receptor to gain viral entry into permissive cells. The binding motif $^{623}$WNNMTWMEW$^{631}$ preferentially uses W over F or Y in all of the $\overline{862}$ $\overline{HIV}$-1 isolates from most of the HIV clades (Dong, 2001). Immunoprecipitation of gp41 from HIV-infected MT4 cells produced a gp41/caveolin-1 compound, confirming direct interaction during infection. Furthermore, development of a vaccine using a 16-residue synthetic peptide to this gp41 region in rabbits led to inhibition of HIV-1, but not HIV-2, infectivity in primary CD4+ T-lymphocytes (Rey-Cuille, 2006). Clearly, the interaction of virus with caveolin-1 is critical to infectivity.

Pathogenic endocytosis through cellular caveolae is proposed to relate to the localization of their cognate receptors within caveolae of the host cell (Shin, 2001). Pathogens currently identified using this pathway include, but are not limited to: *Escherichia coli, Vibrio cholerae* toxin, Simian Virus 40, respiratory syncytial virus, Newcastle disease virus (Cantin, 2007), Japanese encephalitis virus, Echovirus 7, Enterovirus 70, Marburg and Ebola viruses (Bavari, 2002); *Mycobacterium bovis, Campylobacter jejuni, Toxoplasma gondi, Plasmodium falciparum, Chlamydia trachomatis, Mycobacterium kansasii, pneumocustis carinii, Toxoplasma gondii, Clostridium septicum* toxin, Enterobacterial lipopolysaccharide, *Aeromonas hydrophila* toxin, *Helicobacter pylori* toxin and Scrapie prion protein.

Some pathogens are known to assemble within caveolae or lipid rafts. Budding and export are linked with vesicular transport and localize pathogens to vital resources such as cholesterol and signaling pathway proteins. Examples of pathogens currently identified include, but are not limited to: HIV (Nguyen, 2000; Campbell, 2001; Holm 2003); Semliki Forest virus (Lu, 2000); Measles virus (Manie, 2000) and prions (Taylor, 2006).

AIDS (auto immune deficiency syndrome) is characterized by abnormal cytokine levels including interleukin-6 (IL-6); inflammatory protein-10 (IP-10); interferon-gamma (IFN-gamma); and IL-10; as well as monocyte chemoattractant proteins (MCPs); macrophage inflammatory proteins (MIPs); matrix metalloproteinases (e.g., MMP-9 and -2) (Webster, 2006; Kumar, 1999; Conant, 1999); vascular endothelial growth factor (VEGF) and others. These factors have been associated with immunological malfunction, virus-infected cell migration, dementia (leading cause of HIV-1 related death), infection and progression of disease. Cytokines affect production of HIV-1 from primary mononuclear phagocytes (Koyanagi, 1988). Reducing overexpression of select cytokines, such as using MMP inhibitors, have inhibited HIV-associated symptoms such as neurotoxicities (Johnston, 2001).

Cancers of Viral Origin

An estimated 30% of cancers have viral origins, some of which are listed in Table 1.

TABLE 1

Cancers of Viral Origin

| Virus | Type of Cancer |
|---|---|
| Epstein-Barr virus (EBV) | Burkitt's lymphoma |
| | Nasopharyngeal carcinoma |
| | B-cell lymphoma |
| | Hodgkin's disease |
| | Breast cancer (suspected) |

TABLE 1-continued

Cancers of Viral Origin

| Virus | Type of Cancer |
|---|---|
| Hepatitis B virus (HBV) | Liver cancer |
| Hepatitis C virus (HCV) | Splenic lymphoma |
| | Liver cancer |
| Human herpesvirus-8 (HHV-8) | Kaposi's sarcoma |
| | Primary effusion lymphoma |
| | Multicentric Castleman disease |
| Human papillomavirus (HPV) | Cervical, vulvar, vaginal, penile, anal, skin oropharyngeal |
| Human T-cell lymphotrophic virus type 1 (HTLV-1) | Adult T-cell leukemia/lymphoma |
| Simian virus 40 (SV40) | Mesothelioma |
| | Non-Hodgkin's lymphoma, brain and bone tumors, and B-cell lymphomas (suspected) |

BRIEF SUMMARY OF THE INVENTION

The present invention is directed to the modulation of lipid rafts, caveolin proteins, or caveolar functions and processes by platinum(IV) compounds. Caveolae and/or lipid rafts are associated with cell transcription regulation, membrane and cellular transport, cell membrane receptor function, cellular trafficking, antigen presentation, cell differentiation and activation, cytokine modulation, membrane structure, and protein modulation. Caveolae and lipid rafts are known therapeutic targets for numerous biological functions. Diseases and disorders currently known to be therapeutically targeted through caveolae and/or lipid rafts include diabetes, cancer, cardiovascular diseases, atherosclerosis, pulmonary fibrosis, multiple sclerosis, viral and prion diseases, neuronal disorders, degenerative muscular dystrophies, and autoimmune disorders.

DETAILED DESCRIPTION OF PREFERRED EMBODIMENTS

Figure 1A:
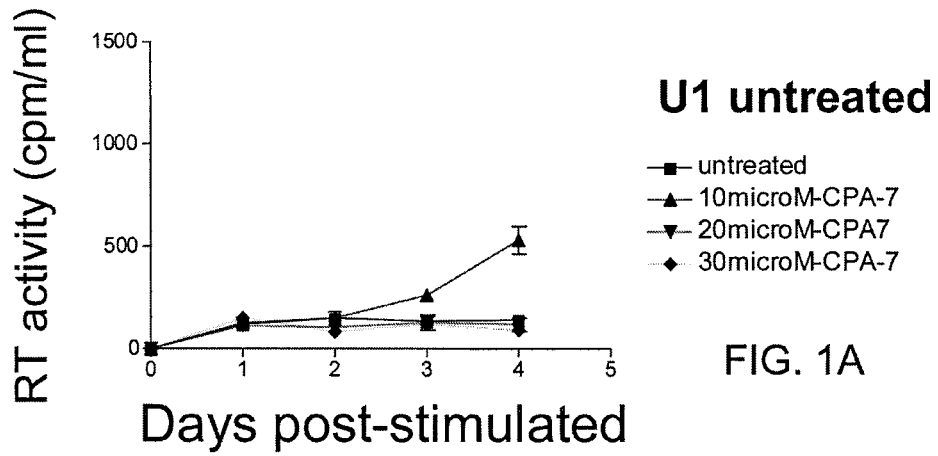
FIGS. 1A-1C illustrate an inhibition of HIV-1 viral replication in chronically-infected U1 promonocytes incubated with platinum(IV) compound, comparing unstimulated U1 (FIG. 1A), TNF-alpha stimulated U1 (FIG. 1B), and IL-6 stimulated U1 (FIG. 1C).
Figure 1B:
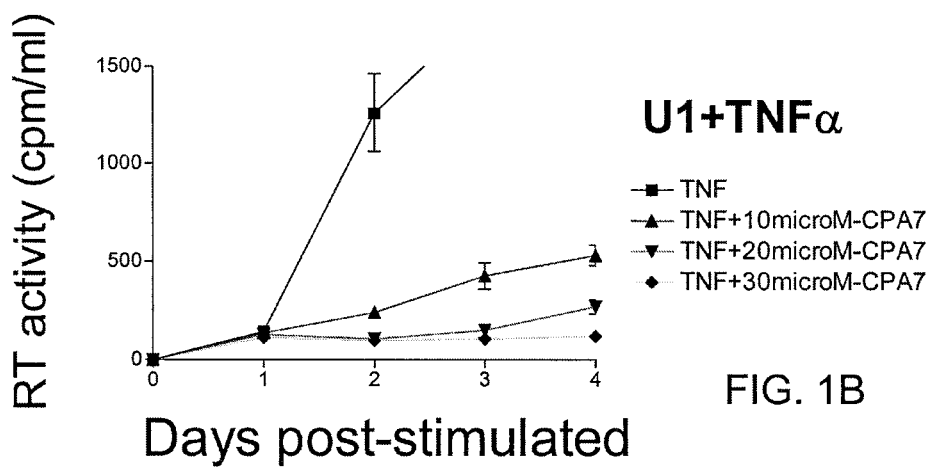

A detailed description of the preferred embodiments of the invention will now be presented with reference to FIGS. 1A-3.

The interactions noted above in the Background between caveolae and metals and compounds suggest potential specific relationships between caveolae and certain metal compounds or metals that are capable of modulating cellular processes associated with caveolae.

Since the aberrant cellular signaling pathways are localized to caveolae through the caveolin scaffolding domain and viral pathways often include caveolae, viral oncogenic potential can be alleviated or prevented with the platinum compounds of the present invention that have also been shown to reduce tumor growth and metastasis.

Cytokine and Chemokine Modulation

Owing to membrane location, transport functions, receptor interactions and signaling pathways, caveolae have the capacity to influence cytokines and chemokines. In murine models, a number of these are modulated when platinum(IV) compounds are administered. These include, but are not limited to: Ribonuclear Protein Antibody; Beta-2 Glycoprotein Antibody (RBM Ratio); CD40 and CD40 ligand; Eotaxin; Fibrinogin; Granulocyte Chemotactic Protein-2; Haptoglobin; Interferon Gamma; Interleukin-10; Interleukin-18; Interleukin-6; Inflammatory Protein-10; Leptin; Lymphotactin; Monocyte Chemoattractant Protein-1, -3, and -5; Macrophage-Derived Chemokine; Macrophage Inflammatory Protein-1alpha, -1beta, -1gamma, -2; Matrix Metalloproteinase-9 and -2; Tissue Inhibitor of Metalloproteinase Type-1; Vascular Cell Adhesion Molecule-1; and Vascular Endothelial Growth Factor. Some disease relationships are outlined in Table 2.

TABLE 2

Disease Relationships Between Antigens And Abnormalities And Diseases

| Antigen | Associated Abnormalities and Diseases or Benefits | | | |
|---|---|---|---|---|
| Beta-2 Glycoprotein Antibody | regulation of coagulation | thrombotic disease | Hughes Syndrome (thrombosis) | Lupus |
| Ribonuclear Protein Antibody | Lupus | connective tissue disease | | |
| CD40 | | arterosclerosis | thrombosis atheroma | |
| CD40 ligand | activation of T-cells; mast and B-cells | | | |
| eotaxin | allergies | dermatitis | asthma | artherosclerosis |
| fibrinogen | thrombosis | | | |
| GCP-2 | arthritis | endometriosis | angiogenesis | |
| haptoglobin | myocardial infarction | pulmonary embolism | hypercholesterolemia | coronary artherosclerosis |
| IL-10 | viral clearance | coronary heart disease | ischemic heart disease | |
| IL-18 | Crohn's Disease | | | |

TABLE 2-continued

Disease Relationships Between Antigens And Abnormalities And Diseases

| Antigen | Associated Abnormalities and Diseases or Benefits | | | | |
|---|---|---|---|---|---|
| IL-6 | coronary heart/ cardiovascular disease | myocardial infarction | angina pectoris, artherosclerosis | diabetes | HIV |
| IP-10 | diabetes | coronary heart disease | viral clearance | | |
| leptin | diabetes | fat metabolism | hyperinsulinemia | | |
| MCP-1 | coronary heart disease | stroke | insulin resistance | HIV dementia | |
| MMP-9 MMP-2 and MT-MMP-1 | cell migration | metastasis | HIV | arthritis | |

Inhibition of TH17 T-Lymphocytes

Produced by a variety of cell types (pleiotropy), predominant cytokine activities are those related to T-lymphocyte cells and macrophages. In a simplified model, T-helper cells begin as THO cells, producing IL-2, IL-4 and IFN-gamma. Increased IL-4 environments transform TH0 to TH2 cells whereas IL-12 leads to TH1 cells. These two groups are broadly antagonistic with TH1 representing pro-inflammatory cellular immunity and TH2 being anti-inflammatory humoral immunity as proposed by the TH1/TH2 homeostasis hypothesis. Imbalances between these responses have been associated with disease conditions, whereby TH1-bias suggests intracellular pathogenic infections or cancer and TH2-bias suggests extracellular (such as parasitic) or allergic reactions. Feedback loops, suppressive effects and receptor expressions add increasing complexity to this model which is receiving refinement on an ongoing basis.

Contributions of T-regulatory (Tregs, also known as TH3) cells, justify new cohorts of TH response. These cells produce both transforming growth factor beta (TGF-beta) and IL-10, related to immunosuppression and self-tolerance. In the last two years, a new phenotype of T-cells has been recognized in mice and humans which produce IL-17 and designated "TH17" T-cells (Afzali, 2007; Veldhoen, 2006; Bettelli, 2007; Mangini, 2007). While some differences are noted between species, the distinguishing feature between TH3 (Tregs) and TH17 subsets largely depends upon the availability of cytokine IL-6, known to be secreted by T-cells and macrophages (antigen-presenting cells). Importantly, pro-inflammatory effects of IL-17 act through ubiquitous IL17R receptors, leading to numerous disorders. Affecting many cell types, IL-17 stimulates production of chemoattractants, pro-inflammatory cytokines, hematopoietic growth factors, the costimulatory molecule ICAM-1; and synergizes with IL-1beta, TNF-alpha, IFN-gamma and CD40L (Afzali, 2007). Other than the predominant $CD4^+$ T-cells source, IL-17 may also be produced by gamma-delta T cells, $CD8^+$ T-cells, eosinophils, neutrophils and monocytes.

In humans, IL-17 contributes to the pathogenetics of rheumatoid arthritis, respiratory diseases, allograft rejection, Lupus, psoriasis, multiple sclerosis and chronic inflammatory bowel disease. In seropositive HIV patients, significantly higher levels of IL-17 as compared to sero-negative controls have been associated with both $CD4^+$ and $CD4^-$ T-cells from peripheral blood mononuclear cells (Maek, 2007). Additionally, it has been reported (Kebir, 2007) that human TH17 lymphocytes can disrupt the blood-brain barrier, kill neurons and cause CNS inflammation. Finally, myelin-phagocytosing macrophages displaying TH2 cytokine signatures invade sciatic and optic nerves in vitro, suggestive of TH17 development (van Rossum, 2008). The recent explosion of papers and research connecting TH17 with neuropathologies strongly justifies the probability of its role in lentiviral-related diseases.

Importantly, caveolin-1 tends to downmodulate interacting proteins interfacing through the "scaffolding domain," thus maintaining a healthy equilibrium and checkpoint. Certain platinum(IV) compounds interacting with caveolin proteins, lipid rafts and/or caveolae also modulate these proteins, thus impacting a host of important cellular functions not limited to cancer therapies. Additionally, evidence of enhanced antigen-presentation, reduced viral production, inhibition of viral infectivity and regulation of cytokine effects identify a broad range of therapeutic applications.

Some platinum(IV) compounds previously shown to inhibit STAT proteins, for instance, do not demonstrate this effect, suggesting specific ligand requirements as well as the +4 oxidation state are required. Platinum(II) compounds tested have been ineffective. Furthermore, the most effective platinum(IV) compounds are those of trans geometries—those found least effective in their corresponding platinum(II) state as anticancer compounds. In addition, no evidence of hematological toxicities is evidenced in vivo by these select platinum(IV) compounds, but rather, a recovery of immunological functions that allow a short treatment period at low doses to result in long term recovery and improved health. Thus these activities of certain platinum(IV) compounds are novel and describe a distinct subset of potential therapeutics useful for diseases and conditions in which modulating caveolar functions will improve health.

Importantly, platinum complexes of the invention reduce IL-6, TNF-alpha and IL-1beta serum measures in vivo, while increasing IL-12. IL-12 suppresses TH17 T-cell differentiation while IL-6 and IL-1beta promote it. TNF-alpha is one of the cytokines produced by TH17 cells. Reducing this T-cell subset population may be useful in the treatment of autoimmune disorders. Thus, inhibition of TH17 T-cell differentiation and their subsequent cytokine production can be achieved using intermittent dosing of this small molecule, without thwarting normal healthful function of the TH17 T-cell subset, nor resulting in myelosuppression.

Example 1

In Vitro Inhibition of HIV Replication

Figure 1C:
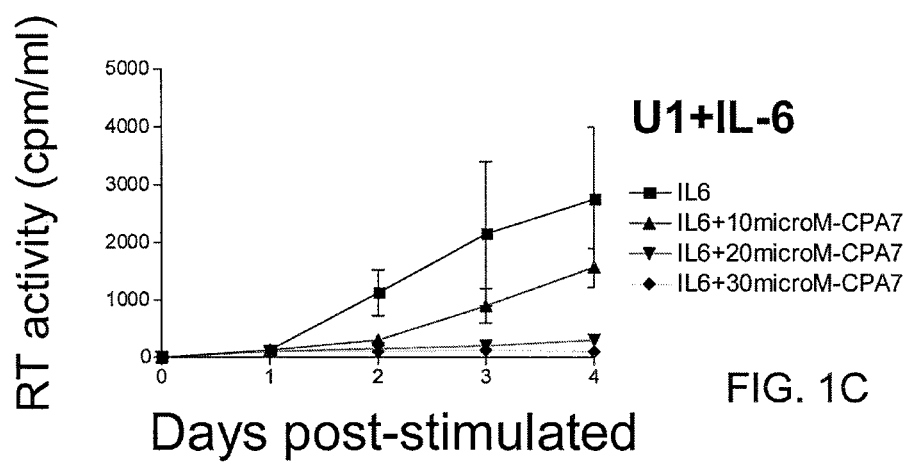

The U1 cell line was derived from U937 promonocytic cells surviving the cytopathic effect associated with the acute infection by HIV-1 LAI/IIIB. U1 cells contain two integrated copies of proviral HIV DNA and are characterized by low constitutive levels of virus expression that can be upregulated by several cytokines and phorbol esters. U1 cells were cultivated at $2\times10^5$ cells per ml in RPMI medium 1640 (M.A. Whittaker Bioproducts, Walkersville, Md.) supplemented with 1 mM HEPES buffer, antibiotics and glutamine plus 10% fetal calf serum (FCS) (Hyclone Laboratories, Logan, Utah), containing less than 7 pg/ml of endotoxin. The cells were cultured in 96 or 48 well flat-bottomed plastic plates (Costar, Cambridge, Mass.) and incubated with the different stimuli at 37° C. in 5% $CO_2$. TNF-alpha (1 ng/mL) (FIG. 1B), or IL-6 (10 ng/mL) (R&D Systems) (FIG. 1C) were added as stimulants for 20 min at 37° C. In addition to the presence or absence of stimulatory cytokines, 10, 20 or 30 µM CPA-7 was added to each culture well (n=3); unstimulated control cells were also tested in the presence or absence of drug (FIG. 1C). Reverse transcriptase (RT) activity was measured between days 1 and 4 as compared with untreated (no CPA-7) cells. 5 µL of U1 supernatants were added, in duplicate, to 25 µL of a mixture containing poly(A), oligo(dT) (Pharmacia, Piscataway, N.J.), $MgCl_2$ and $[^{32}P]$-labeled deoxythymidine 5'-triphosphate (dTTP) (Amersham, Arlington Heights, Ill.) and incubated for 2 h at 37° C. Then, 6 µL of the mixture was spotted onto DE81 paper (Whatman International, Maidstone, UK), air-dried, washed five times in 2× standard saline citrate buffer, and two additional times in 95% ethanol. The paper was then dried, cut, and counted in a Beckman LS 5000 scintillation counter. RT activity was measured in counts per minute (cpm)/mL. It should be noted that $Pt(IV)Cl_4$, a known STAT3 inhibitor, did not inhibit viral replication in parallel assays.

Example 2

Topical Application and Inhibition of Tumor Transformation

Figure 2:
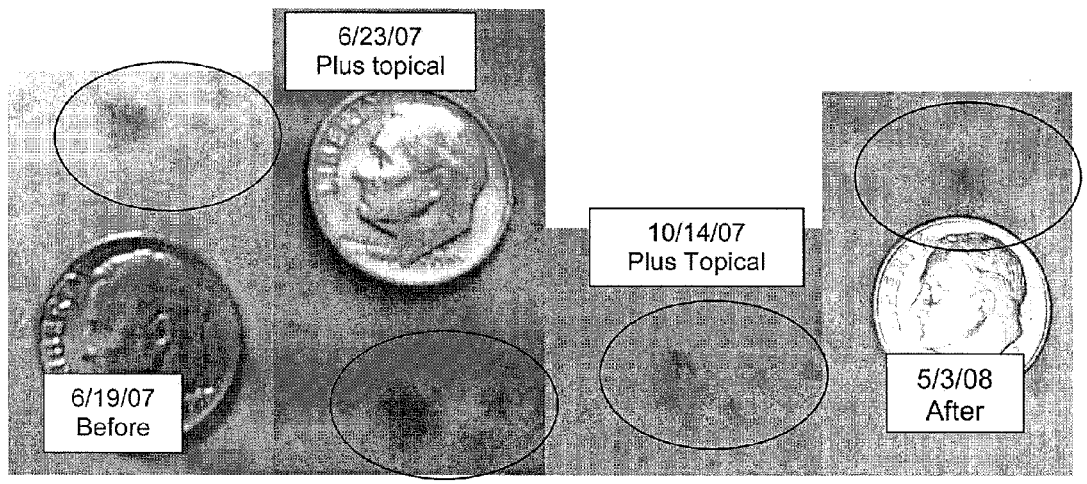
FIG. 2 illustrates the effect of topical application of platinum(IV) compound in reducing the appearance of cell transformation.
Figure 3:
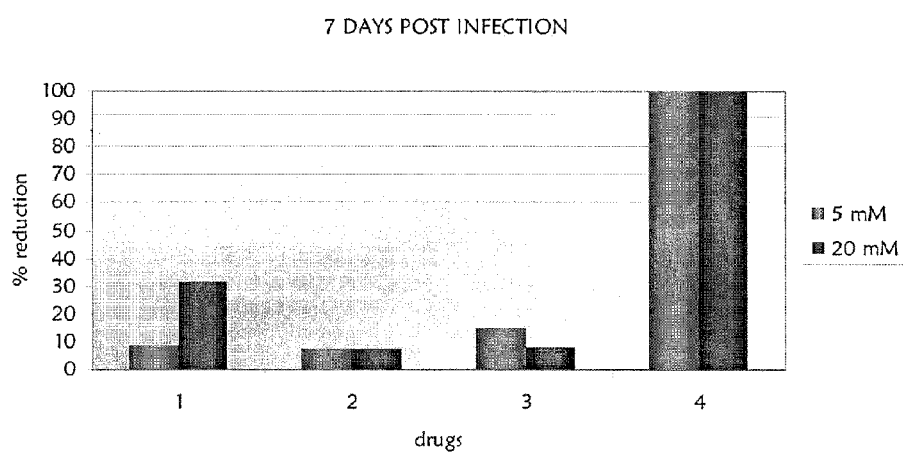
FIG. 3 plots the comparative percent viral inhibition by four platinum compounds as measured by optical density of p25 antigen relative to controls.

FIG. 2 illustrates a skin mole, initially presenting as asymmetric, bumpy and with multiple colors. A solution of $1.0\times10^{-3}$ M CPA-7 was applied topically to the mole with a Q-tip on three occasions (Jun. 19, 2007; Jun. 23, 2007, and Oct. 14, 2007). The mole became darker (June 23) and scabbed, with the scab peeling off spontaneously. Notice the three freckles to the right identify the same mole. Almost one year later (May 3, 2008), the mole continues to look healthy. While the mole itself became scabbed, there was no itching, burning, or discomfort of any kind.

Example 3

Sucrose Gradient Separation and Identification of Platinum in Caveolar Fractions A549 Human lung adenocarcinoma cells were maintained in a 1:1 mixture of Dubelco's Modified Eagle Medium-high glucose (DMEM-Gibco) and F-12 nutrient mixture (Gibco) supplemented with 10% fetal bovine serum (FBS) (Biowhittaker) and 100 u/mL penicillin-streptomycin (Biowhittaker). Cells were maintained in culture flasks incubated at 37° C. and 5% $CO_2$. These were exposed to 20 µM CPA-7 for 8 h. To harvest, cells were loosened with trypsin-versene, collected and centrifuged. After 3 washes with media, cells were frozen with 10% DMSO until analyzed.

Caveolae were isolated essentially as follows: Cells were homogenized in 2 ml MBS buffer (25 mM morpholinoethane sulfonic acid, pH 6.5, 0.15M NaCl, 1% Triton X-100, and 1 mM PMSF) using a motor-driven Teflon glass Thomas homogenizer, which has a serrated pestle. Two ml of 80% sucrose in MBS without Triton X-100 was then added and the homogenate was placed in a 3½×9/16-in. polyallomer centrifuge tube. This was carefully overlaid with 4 ml of 20% sucrose in MBS without Triton X-100 and 4 ml of 5% sucrose in MBS without Triton X-100. The discontinuous gradients were centrifuged at 39,000 rpm for 16 h in a SW41 rotor at 4° C. The gradients were fractionated into 1-ml fractions. The protein in these fractions was precipitated by the addition of 4 volumes of methanol and centrifugation at 9000 g for 10 min. The pellets were resuspended in minimal volumes of 1% SDS depending on the protein concentration of each fraction. The concentration of protein in each fraction was determined by the BCA protein assay from Pierce. Caveolin proteins were detected to be greatest in fraction 5, declining in subsequent fractions. Supernatant, after protein precipitation was reserved.

Individual fractions were collected in 1-mL microtubes. To each tube was added an 8 M solution of nitric acid, dropwise, with gentle heating in a water bath, to digest the sample. A few drops of 30% $H_2O_2$ were added as needed to facilitate digestion of lipids. Following digestion (disappearance of all solids, 2 days) each microtube was filled with water to approximately the same level and mixed on a vortex stirrer. Samples were then analyzed by graphite furnace atomic spectroscopy.

Platinum analysis was performed using a graphite furnace atomic absorption spectrophotometer with a 265.9 nm source (Ultra Pt), 0.2 nm slit width, background correction on. UHP Argon was the flow gas. Two readings were made for each measure. To remove solvents, additional time was programmed at 1000° C.; two samples of 20 µL were deposited, with a drying step between, to concentrate sample. Five standard concentrations of Pt created a linear calibration curve. Pt signal was measured for absorbance at peak height. A summary of the data is provided in Table 3.

TABLE 3

| | Platinum Concentration (µg/L) | | |
|---|---|---|---|
| Fraction Number | Before PPT* | Protein PPT* | Supernatant |
| 1 | 11.8 | 15.6 | 14.1 |
| 2 | 9.9 | 6.7 | 6.4 |
| 3 | 4.0 | 5.1 | 4.1 |
| 4 | 3.2 | 5.4 | 0.8 |
| 5 | 3.1 | 15.8 | 0.4 |
| 6 | 2.2 | 3.1 | 0.4 |
| 7 | 1.9 | 3.5 | 2.9 |
| 8 | 1.2 | 1.1 | 1.6 |
| 9 | 1.5 | 1.1 | 1.2 |
| 10 | 1.6 | 0.8 | 0.4 |
| 11 | 1.6 | −0.1 | 3.1 |
| 12 | 1.8 | 0.3 | 1.6 |
| 13 | 1.0 | 0.1 | (no data) |

*(PPT = precipitation)

Highest concentrations are marked in bold for the first (lipid rafts) and fifth (caveolin protein) fractions. It should be noted that "Protein PPT" tubes contained 50 µL after precipitation (PPT) and re-solvation; "Before PPT" tubes contained 200 µL. Therefore, a reading four times greater for "Protein PPT" tubes over "Before PPT" tubes is reasonable. "Supernatant" samples represent Pt that did not associate with protein following precipitation step. The data clearly show that the two fractions representing lipid rafts (fraction 1) and caveolae with caveolin proteins (fraction 5) are those containing the most Pt drug.

Example 4

Inhibition of Cancer Cell Growth in Tissue Culture Assays

Crandall Feline Kidney Fibroblast Cells (CrFK)—ATCC number: CCL-94

CrFK cells (cortical epithelial cells, adherent) were grown in Eagle's minimal essential medium supplemented with 10% fetal bovine serum 2 mM Glutamine (Sigma-Aldrich, Milan, Italy), 100 U/mL penicillin and 100 ug/mL Streptomycin. CrFK cells are incubated at 37° C. in 5% $CO_2$.

Growth inhibition was tested by exposing the cell cultures (in triplicate and cultivated in above medium) to 5 or 20 μM each of four platinum drugs (#1-4) and comparing their viabilities using propidium iodide exclusion testing. Each reading was compared against control cells without drug. Table 4 summarizes the readings on days 2 and 5 compared with drug-free controls (K- and K-IP). Drugs are identified as: CPA-7 (#1); NAD (#2); cisplatin (#3), and FX101 (#4). Drugs #1, #2 and #4 are Pt(IV)'s while drug 3 is a Pt(II). Both drugs #1 and #2 have been shown to inhibit STAT3.

TABLE 4

CrFK Growth Inhibition Test (Propidium Iodide)

| CrFK | | 2 | 5 | days post administration |
|---|---|---|---|---|
| 20 μM | K- | 1.01 | 5.23 | % |
| | K- IP | 2.04 | 7.74 | % |
| | #1 | 28 | 19.3 | % |
| | #2 | 7 | 4.2 | % |
| | #3 | 20 | 11.82 | % |
| | #4 | 15 | 5.6 | % |
| 5 μM | #1 | 14 | 13.9 | % |
| | #2 | 8 | 4.2 | % |
| | #3 | 9.2 | 7.1 | % |
| | #4 | 7.3 | 4.2 | % |

MBM Lymphoid T-Cell Line

This IL-2 dependent feline T-lymphoblastoid cell line has been derived from peripheral blood mononuclear cells (PBMC: pan-T+; CD4-, CD8-, concanavalin A-dependent) of an FIV- and feline leukemia virus-negative SPF cat (Matteucci, 1995). The MBM cell line has been phenotyped as CD3+ CD4- CD8- by use of appropriate anti-feline sera; and is grown in RPMI 1640 medium supplemented with 10% fetal bovine serum, 5 μg/mL concanavalin A (Sigma-Aldrich, St. Louis, Mo.), 20 U/mL recombinant human interleukin-2 (Roche, Milan, Italy); and cultivated at 37° C. in 5% $CO_2$.

Growth inhibition was tested by exposing the MBM cells (in quadruplicate and cultivated in above medium) to 5 or 20 μM each of four drugs (#1-4) and comparing their viabilities using propidium iodide exclusion testing. Each reading was compared against control cells without drug (Table 5). Growth inhibitions here are much higher than for CrFK cells, suggesting lymphoid cell lines can be targeted well by these compounds. Drugs are identified as: CPA-7 (#1); NAD (#2); cisplatin (#3), and FX101 (#4).

TABLE 5

MBM Growth Inhibition Test (Propidium Iodide)

| | MBM | 2 | 5 | days post administration |
|---|---|---|---|---|
| 20μM | K- | 1.01 | 1 | % |
| | K- IP | 5.6 | 3.7 | % |
| | #1 | 60 | 49 | % |
| | #2 | 40 | 17 | % |
| | #3 | 50 | 10 | % |
| | #4 | 45 | 12.4 | % |
| 5μM | #1 | 30 | 7 | % |
| | #2 | 37 | 14.3 | % |
| | #3 | 51.5 | 10 | % |
| | #4 | 38.5 | 15 | % |

Example 5 p25 Antigen Evaluation of Antiviral Activity in MBM Cells

Antiviral activity in MBM was determined by inoculating 200 Tissue Culture Infectious Doses 50% FIV Petaluma (Talbott, 1989) in 100 μL RPMI 1640 medium into quadruplicate wells of 96-well microplates containing $2 \times 10^5$ cells in 100 μL medium. The cultures were monitored by measuring FIV p25 capsid protein (Lombardi, 1994) release in the supernatants after 7 days of incubation at 37° C. in 5% $CO_2$ (Table 6 and FIG. 3). Half the media (without drug) was replaced on days 2 and 6 after infection and initial drug exposure. This reduces the actual contact time with drug as the experiment progresses, suggesting an early time cellular event leading to the observed responses. At 7 days, drug #4 completely eliminated (100%) all measures of virus at both concentrations used, 5 and 20 μM; drug #1 resulted in <30% inhibition by day 7. Drugs are identified as: CPA-7 (#1); NAD (#2); cisplatin (#3) and FX101 (#4). Drugs #1, #2 and #4 are Pt(IV)'s while drug 3 is a Pt(II). Both drugs #1 and #2 have been shown to inhibit STAT3, yet are either completely ineffective (#2) or insignificantly effective (#1). A minimum of 50% inhibition in vitro is required to offset viral infectivity and replication in vivo. These data demonstrate significant differences between Pt(IV) compounds, suggesting that select ligands and their orientations with respect to the octahedral geometry of Pt(IV) compounds define a distinct subset of effective compounds.

TABLE 6 p25 Viral Antigen Measured by OD
P25 (OD) 7 DAYS POST INFECTION

| Drug # | | 1 | 2 | 3 | 4 |
|---|---|---|---|---|---|
| | | conc 5 μM | | | |
| | | 1.093 | 1.06 | 1.04 | 0 |
| | | 1.122 | 1.136 | 1.021 | 0 |
| | | 1.068 | 1.113 | 0.986 | 0 |
| | average | 1.0943 | 1.103 | 1.0157 | 0 |
| | std dev | 0.0221 | 0.0318 | 0.0224 | 0 |
| | | conc 20 μM | | | |
| | | 0.788 | 1.13 | 1.014 | 0 |
| | | 0.825 | 1.099 | 1.033 | 0 |
| | | 0.836 | 1.081 | 0.993 | 0 |
| | average | 0.8163 | 1.1033 | 1.0133 | 0 |
| | std dev | 0.0205 | 0.0202 | 0.0163 | 0 |

K+ = 1.195 (OD of virus-infected control cells)
K- = 0.08 (OD of non-infected control cells)

Example 6

Feline Immunodeficiency Virus Study

Eight 11-year-old specific-pathogen-free domestic female cats infected 6 years ago with the Petaluma strain of FIV were used in this study. The animals were housed individually in a climatized animal facility in accordance with European Community Guidelines, had ad libitum access to fresh water and a proprietary brand of cat food, and were sedated with Tiletamine/Zolazepam intramuscularly prior to any procedure. Three weeks before initiation of the experiment and at scheduled times (Table 7) prior to therapeutic doses, the animals were bled (jugular vein, 8 mL) for hematochemical analyses and circulating lymphocyte subset counts. No local reactions or adverse clinical signs due to treatments were observed during the complete study. The cats weighed from 3-5 kg each. The natural history of infection is well documented for these cats. They were monitored at least once monthly during the first year of infection, once every 3 months during the second year and twice yearly thereafter. The infection has been chronic steady state since the end of 2003.

Two pretreatment blood samples were drawn three weeks apart to serve both as baseline measures and for matching purposes in assigning groups. Measures of virological and immunological parameters included plasma RNA viremia; proviral load in Peripheral Blood Mononuclear Cells (PBMC); as well as numbers of circulating $CD4^+$ and $CD8^+$ T-lymphocytes at scheduled times (Table 7); complete blood count (CBC) profiles were also obtained.

TABLE 7

Blood Sampling and HK Drug Administration Schedule

| | Treatment | | | | | | | | | |
|---|---|---|---|---|---|---|---|---|---|---|
| | August | | | | September | | | | | October |
| | $2^{nd}$ | $23^{rd}$ | $27^{th}$ | $30^{th}$ | $3^{rd}$ | $6^{th}$ | $10^{th}$ | $13^{th}$ | $17^{th}$ | $20^{th}$ | $4^{th}$ |
| HK | | | X | X | X | X | X | X | X | X | |
| Blood sample | Bs* | Bs* | | X | | X | | | | X | X |

*Baseline sample

Drug Preparation 0.1664 g FX101 was dissolved into 30 mL 15% DMSO/PBS and stirred overnight. This solution was sterile-filtered using a 20-mL syringe fitted with a 0.2 µM Sarstedt filter. Each dose was administered under anesthesia, a 1.5 mL venous injection using a 2.5 mL syringe fitted with a 22 G 1¼-in. needle (latex free). Feline BR weighed 3.2 kg at the start of the experiment and CF weighed 2.8 kg. Each received 8.3 mg drug with each dose, so dosages were 2.6 mg/kg for BR and 3.0 mg/kg for CF.

CBC Measures

The hematological counts were performed with EDTA blood using the QBC-Vet Autoread Hematology System counter (IDEXX Laboratories Inc., Westbrook, Me., USA). This system measures hematocrit, hemoglobin concentration, and number and percent of total leukocytes, granulocytes, combined lymphocytes and monocytes, eosinophils platelets, and reticulocytes.

The control feline experienced a kidney infection prior to the September 6 sample; the BR feline experienced a uterine infection (documented history, ongoing) prior to the October 4 sample. These data are noted in the tables. Table 8 summarizes total WBCs over time for each feline. Absence of increased myelosuppression attributable to drug treatment is noted, recognizing that these felines presented with severe immunological impairments. Initially presenting with both leukopenia (<5500 cells/µL) and lymphopenia (<1500 cells/µL), both conditions persisted throughout the study with slight fluctuations. However, the absence of anemia (defined by <24% hemtocrit, Table 11) and thrombocytopenia (defined by <150,000 platelets, Table 12) were noted. While not necessarily indicative of disease progression, all these measures are therapeutically important and suggest an avoidance of immunosuppressive mechanisms typically associated with platinum therapeutics.

TABLE 8

Total White Blood Cell Counts
Unaffected by Drug Treatment (Counts/µL)

| | Baseline Measures | | Treatment Measures | | | Post Measures | |
|---|---|---|---|---|---|---|---|
| | 2-Aug | 23-Aug | 30-Aug (+7 d) | 4-Sep (+12 d) | 20-Sep (+28 d) | 4-Oct (+42 d) | 20-Oct (+58 d) |
| Control (infected) | — | 3900 | 4700 | 7900* | 2300 | 2500 | — |
| HK Inhibitor (cat BR) | — | 5200 | 4600 | 4300 | 3800 | 15500* | — |
| HK Inhibitor (cat CF) | — | 4800 | 4400 | 4500 | 4200 | 4800 | — |

*indicates local infection, unrelated to treatment

TABLE 9

Total Lymphomonocyte Counts
Unaffected by Drug Treatment (Counts/µL)

| | Baseline Measures | | Treatment Measures | | | Post Measures | |
|---|---|---|---|---|---|---|---|
| | 2-Aug | 23-Aug | 30-Aug (+7 d) | 4-Sep (+12 d) | 20-Sep (+28 d) | 4-Oct (+42 d) | 20-Oct (+58 d) |
| Control (infected) | — | 1300 | 2000 | 1800* | 1000 | 1300 | — |
| HK Inhibitor (cat BR) | — | 1000 | 1800 | 1200 | 1100 | 1400* | — |
| HK Inhibitor (cat CF) | — | 1300 | 1300 | 1400 | 1300 | 1500 | — |

*indicates local infection, unrelated to treatment

TABLE 10

Granulocytes (Neutrophils)
Unaffected by Drug Treatment (Counts/µL)

| | Baseline Measures | | Treatment Measures | | | Post Measures | |
|---|---|---|---|---|---|---|---|
| | 2-Aug | 23-Aug | 30-Aug (+7 d) | 4-Sep (+12 d) | 20-Sep (+28 d) | 4-Oct (+42 d) | 20-Oct (+58 d) |
| Control (infected) | — | 2600 | 2700 | 6100* | 1300 | 1200 | — |
| HK Inhibitor (cat BR) | — | 4200 | 2600 | 3100 | 2700 | 14100* | — |
| HK Inhibitor (cat CF) | — | 3500 | 3300 | 3100 | 2900 | 3300 | — |

TABLE 10-continued

Granulocytes (Neutrophils)
Unaffected by Drug Treatment (Counts/μL)

| | Baseline Measures | | Treatment Measures | | | Post Measures | |
|---|---|---|---|---|---|---|---|
| | 2-Aug | 23-Aug | 30-Aug (+7 d) | 4-Sep (+12 d) | 20-Sep (+28 d) | 4-Oct (+42 d) | 20-Oct (+58 d) |

*indicates local infection, unrelated to treatment

TABLE 11

Hematocrit (% Red Blood Cell Hemoglobin)
Unaffected by Drug Treatment

| | Baseline Measures | | Treatment Measures | | | Post Measures | |
|---|---|---|---|---|---|---|---|
| | 2-Aug | 23-Aug | 30-Aug (+7 d) | 4-Sep (+12 d) | 20-Sep (+28 d) | 4-Oct (+42 d) | 20-Oct (+58 d) |
| Control (infected) | — | 29 | 30 | 31* | 21 | 21 | — |
| HK Inhibitor (cat BR) | — | 27.1 | 21.1 | 25 | 25.2 | 16.5* | — |
| HK Inhibitor (cat CF) | — | 28.2 | 23.8 | 23.4 | 24.8 | 27.4 | — |

*indicates local infection, unrelated to treatment

TABLE 12

Absence of Thrombocytopenia (Platelets < 150,000)
Due to Drug Treatment (in Thousands of Counts/μL)

| | Baseline Measures | | Treatment Measures | | | Post Measures | |
|---|---|---|---|---|---|---|---|
| | 2-Aug | 23-Aug | 30-Aug (+7 d) | 4-Sep (+12 d) | 20-Sep (+28 d) | 4-Oct (+42 d) | 20-Oct (+58 d) |
| Control (infected) | — | 126 | 148 | 144* | 176 | 165 | — |
| HK Inhibitor (cat BR) | — | 212 | 157 | 215 | 210 | 110* | — |
| HK Inhibitor (cat CF) | — | 168 | 196 | 195 | 178 | 158 | — |

*indicates local infection, unrelated to treatment

Plasma RNA Viremia

Viral RNA extracted from plasma using the QIAmp viral RNA kit (Qiagen), was reverse transcribed and amplified by reverse transcription TaqMan polymerase chain reaction (TM-PCR). Reverse transcription and amplification conditions, and minimum detection limits of the assay (200 copies/mL plasma) are described elsewhere (Pistello, 2005). This measure represents viral presence in circulation, reflecting potential infectivity and productive synthesis of viral particles.

Table 13 illustrates measures of plasma viremia from the two test cats, "BR" and "CF" at scheduled times following Table 7. Each of these samples was taken immediately prior to drug injection for the scheduled dosing, August 23-September 30. This provided two pretreatment samples as baseline measures, 3 samples during treatment, and two post-treatment samples; note the addition of an unscheduled sample October 20. A significant reduction in plasma viremia occurred in both cats over two weeks until measures were below detection for the remaining duration of treatment. Following the last dosage, the first post-treatment results were ambiguous, with one cat experiencing a strong rebound and the other remaining below detection. This difference may be attributable to a uterine infection experienced by cat "BR" at this time—a historically frequent occurrence for this cat. It is well known that lipopolysaccharides (LPS) induce lentiviral replication, and this may therefore be related. Cat "CF" continued to show low levels of viremia, and both cats demonstrated significantly lower viremia as compared with baseline measures even 4 weeks to 9 months past the final dosage, in the absence of additional therapies. This recovery suggests the drug acts as an immune adjuvant, acting in vivo.

TABLE 13

Plasma Viremia
(Number of viral RNA copies/mL plasma)

| | Baseline Measures | | Treatment Measures | | | Post Measures | | |
|---|---|---|---|---|---|---|---|---|
| | 2-Aug | 23-Aug | 30-Aug (+7 d) | 4-Sep (+12 d) | 20-Sep (+28 d) | 4-Oct (+42 d) | 20-Oct (+58 d) | 15-May (+9 mos) |
| HK Inhibitor (cat BR) | 4282 | 6974 | 1249 | <100 | <100 | 10517 | 1057 | <1000 |
| HK Inhibitor (cat CF) | 2582 | 8841 | 1300 | <100 | <100 | <100 | 898 | <1000 |

*Treatment period 23-Aug to 20 Sep. 2007

Proviral Load (in Primary Blood Mononuclear Cells)

Genomic DNA was extracted from the PBMC using the QIAamp DNA Blood Mini kit (QIAGEN). Proviral DNA was quantified from 0.4 ug genomic DNA by TM-PCR under the same conditions used for cDNA amplification except that the reaction mixture volume was 25 μl. The sensitivity of the assay was 100 copies/ug genomic DNA (Pistello, 2005). This measure reflects viral integration into the host PBMCs, primed for production of viral particles with commencement of transcription. It is highly noteworthy that the proviral load reduced significantly even long after final treatment (+9 months). This is indicative of viral clearance and immune recovery, including apoptotic elimination of virally-infected cells. Viral reservoirs, such as those of macrophages and monocytes, have prevented eradication of lentiviruses (Nicastri, 2008).

TABLE 14

Proviral Load in PBMC
(Number proviral DNA copies/μg genomic DNA)

| | Baseline Measures | | Treatment Measures* | | | Post Measures | | |
|---|---|---|---|---|---|---|---|---|
| | 2-Aug | 23-Aug | 30-Aug (+7 d) | 4-Sep (+12 d) | 20-Sep (+28 d) | 4-Oct (+42 d) | 20-Oct (+58 d) | 15-May (+9 mos) |
| HK Inhibitor (cat BR) | 8560 | 6867 | 6476 | 1048 | 4660 | 14724 | 2790 | <1000 |
| HK Inhibitor (cat CF) | 4148 | 4472 | 5803 | 6738 | 4152 | 14500 | 4211 | <1000 |

*Treatment period 23-Aug to 20 Sep. 2007

Circulating CD4+ and CD8+ T-lymphocytes

Numbers of peripheral CD4+ and CD8+ T-lymphocytes in the blood were determined by labeling with mouse monoclonal antibodies to feline CD4+ (FE1.7B12) and feline CD8+ (FE1.10E9), obtained from Peter F. Moore, University of California, Davis, Calif. Bound primary antibodies were detected using FITC-conjugated anti-mouse IgG1 (Space-Serotec, Milan, Italy), and the samples were analyzed on a FACScan flow cytometer (Becton Dickinson, San Jose, Calif.). Both a negative (no drug) and positive (integrase inhibitor cocktail) control are included with data from two HK inhibitor-tested felines. Final CD4+/CD8+ ratios remained higher in both tested felines as compared with controls at the conclusion of this study.

TABLE 15

Relative CD4+/CD8+ T-Lymphocyte Counts in Cats
Receiving HK Inhibitor vs. Positive
(HAART drugs) and Negative Controls

|  | Baseline Measures | | Treatment Measures | | Post Measure |
| --- | --- | --- | --- | --- | --- |
|  | 2-Aug. | 23-Aug. | 30-Aug. | 4-Sep. | 4-Oct. |
| HK Inhibitor (cat BR) | 1.1 | 1.2 | 1.5 | 1.53 | 1.9 |
| HK Inhibitor (cat CF) | 1.3 | 1.23 | 1.3 | 1.6 | 1.4 |
| Negative Control | 1.0 | 0.93 | 0.97 | 1.1 | 1.1 |
| Positive Control (HAART) | 0.76 | 0.80 | 1.0 | 1.4 | 0.73 |

Example 7

Feline Blood Serum Measures Following Treatment

Test sera samples from select felines were analyzed using the Rules-Based Medicine (Austin, Tex.) human multi-analyte for 90 measures from a single sample of less than 0.5 mL. The assay uses immunofluorescent beads to simultaneously measure antibody recognition to individually identifiable colored beads, each conjugated with a specific antibody, within a single well plate. Blood samples were drawn preceding (pretreatment) and following (post treatment) one-month HK Inhibitor treatment (from felines in Example 6), and are compared with two uninfected control felines. Human cross-reactive antibodies are commonly used for felines, and are relative rather than quantitative measures. Reductions in TNF-alpha and MMP-2 are evident in treated cats; TIMP-1 (Tissue Inhibitor of Metalloproteinases) is not associated with the downregulation of MMP-2. Both MMP-2 and MMP-9, as well as MCP-1, are considered important contributors to the penetration of virally-infected cells across the BBB (Webster, 2006). Reduced TNF-alpha together with increased IL-12 are indicative of attenuated TH17 lymphocyte capacities, the former associated with cytokine production and the latter with inhibition of cell subset differentiation (Annunziato, 2007). Additional comments follow the table.

TABLE 16

Relative Blood Serum Measures from Felines
by Immunofluorescent Bead Analysis

|  | Calcitonin (pg/mL) | IL-13 (pg/mL) | CD40L (ng/mL) | IL-8 (pg/mL) | TNF-alpha (pg/mL) | IL-12p70 (pg/mL) | MMP-2 (ng/mL) | TIMP-1 (ng/mL) |
| --- | --- | --- | --- | --- | --- | --- | --- | --- |
| Control 1 (uninfected) | <6.0 | 26 | 0.036 | <3.5 | 1.9 | 15 | <LOW> | 6.8 |
| Control 2 (uninfected) | <6.0 | 22 | 0.054 | <3.5 | 2.4 | 19 | <LOW> | 8.0 |
| Cat BR pretreatment | 7.6 | 15 | 0.036 | <3.5 | 1.3 | 22 | 3000 | 6.5 |
| Cat CF pretreatment | 11 | 12 | 0.029 | <3.5 | 1.0 | 31 | 3150 | 9.8 |
| Cat BR post treatment | 2.9 | 27 | 0.017 | 4.1 | 0.91 | 38 | 2070 | 9.0 |
| Cat CF post treatment | 2.9 | 34 | 0.0067 | 5.7 | 0.57 | 51 | 2120 | 7.3 |

CD40L:

CD40L (sCD40L) in paired samples of plasma and cerebrospinal fluid obtained from 25 HIV-infected individuals is significantly higher in both for cognitively impaired patients as compared with their unimpaired counterparts. CD40 signaling in microglia and monocytes synergizes with effects of TNF-alpha and lentiviral Tat proteins, amplifying inflammatory processes within the CNS and influencing neuronal survival (Sui, 2007).

IL-8:

Interleukin-8 (CXCL8) is a CXC chemokine of the innate immune system primarily related to the recruitment of neutrophil granulocytes, thus also known as Neutrophil Chemotactic Factor. It is produced by macrophages, endothelial and epithelial cells; while other cells such as macrophages, mast cells, keratinocytes and endothelial cells are also responsive to it, through CXCR1 and CXCR2 receptors. Some of these productions are therefore self-regulating. IL-8 presents both as homodimers and monomers.

Decreased levels of IL-8 production in HIV-1 subjects have been measured. Notably, the reduced levels may increase susceptibility to pneumococcal infection in HIV-infected subjects (Gordon, 2005). IL-8 and RANTES (regulated upon activation normal T cell expressed and secreted) have been shown to suppress HIV-1 replication in macrophages, together with reducing the CCR5 receptor availability and sensitivity—CCR5 is a coreceptor for HIV-1 R5 variant infection (Csoma, 2006). Furthermore, patients identified to control virus replication during periods of structured HAART treatment interruptions and long-term nonprogressors (LT-NPs) exhibit greater CD8+ T-cell responsiveness to IL-8 through expression of CXCR1; contrastingly, this receptor was found to be downregulated during periods of uncontrolled viral replication in vivo. Therefore, IL-8/CXCR1CD8+ T-cell cytotoxic potential may effectively control HIV-1 replication (Hess, 2004).

TIMP-1:

Tissue Inhibitor of Metalloproteinases, is usually inversely related to MMP activities, but cannot account for the change in MMP-2 in these data.

Calcitonin is a protein produced primarily by the parafollicular (also known as C-cells) of the thyroid, and in many other animals in the ultimobranchial body. It acts to reduce blood calcium ($Ca^{2+}$), opposing the effects of parathyroid hormone. Procalcitonin is a prohormone of calcitonin; both have been identified as monocyte chemoattractants (Wiedermann, 2002). Serum procalcitonin levels are markedly elevated in sepsis and correlate positively with severity (Sexton, 2008). Procalcitonin concentrations distinguish between bacterial and viral infections, being lower in viral infections and inflammatory diseases. These increased levels in FIV-infected felines, therefore, may be more indicative of BBB penetration in late-stage lentiviral infections.

IL-12p70:

During early infection, HIV-infected individuals have higher numbers of virus-specific cytotoxic T lymphocytes (CTLs) that initially reduce the viral load but later fail. Dysregulation of cytokines like interleukin-12 (IL-12) result from the interaction of HIV-1-specific T cells with antigen-presenting cells, resulting in CTL dysfunction. Secretion of IL-12 is reduced as HIV progresses, correlating with impaired CTL function (Gupta, 2008). Data suggest a role of IL-12 in priming CD4(+) T cells to stimulate CD8(+) T cells. In addition, IL-12 can downregulate a constitutively active G protein-coupled receptor that contributes to the development of Karposi's sarcoma in AIDS patients (Yarchoan, 2007). Functional IL-12(+) dendritic cells may stabilize HIV disease progression (Daniel, 2008). Impaired response of Natural Killer cells in HIV-progressors as compared to LTNP's and HIV-negative donors correlates with a decreased production of IL-12 (Saez, 2007).

TNF-Alpha:

Tumor Necrosis Factor-alpha is secreted by macrophages, monocytes, neutrophils, T-cells and NK-cells in response to different stimuli including interferon, IL-2, GM-CSF (granulocyte macrophage colony-stimulating factor) and others. Its production typically increases with the progression of HIV/AIDS, and is hypothesized to act via lipid raft-dependent stimulation of the HIV-1 provirus present in such cellular reservoirs as mononuclear phagocytes (Herbein, 2008). Human brain microvascular endothelial cells (HBMEC) exposed to HIV-1-infected macrophages increase expression of tumor necrosis factor-alpha-induced proteins, interferon (IFN)-inducible genes, intercellular adhesion molecule-1, transcription factors of the nuclear factor-kappaB family, and signal transducer and activator of transcription-1, leading to BBB (blood-brain-barrier) impairment (Chaudhuri, 2008).

IL-13:

Both IL-4 and IL-13 downregulate expression of the monocyte receptor CXCR4, while IL-13 also downregulates CCR5; both these receptors are utilized by lentiviral infections. Additionally, both IL-4 and IL-13 inhibit virus replication in monocytes (Creery, 2006). Acute exposure of PBMCs derived from HIV-infected subjects to IL-13 increased recall T cell lymphoproliferative responses against antigens through enhanced antigen presentation together with increased CD86 (B7.2) expression (Papasavvas, 2005). This T-cell activation and survival may also be evidenced in the CD4+/CD8+ ratios of Table 15 of Example 6.

Matrix Metalloproteinases (MMPs):

MMPs include 23 human types, identified by number and/or other names. While their overall function relates to extracellular matrices such as collagens, they are also important in angiogenesis, antigen processing and presentation, inflammation, chemokine/cytokine regulation, and other physiological functions. Dysfunction in MMPs has been identified for diseases including arthritis, cirrhosis, glaucoma, lupus, multiple sclerosis and HIV-1 associated dementia (Webster, 2006).

Of special interest are the gelatin-binding metalloproteinases, MMP-2 and MMP-9 (Gelatinases A and B, respectively). These have a unique fibronectin-repeat catalytic domain, a standard prodomain, which initially folds over a $Zn^{2+}$ catalytic site, and a $Ca^{2+}$-containing homopexin-like carboxyl end related to substrate specificity. MMPs are normally regulated. However, HIV infection of monocytes and macrophages generally results in elevations of both MMP-2 and MMP-9 and reduction in their regulators, tissue inhibitors of metalloproteinases, TIMPs (Webster, 2006). Experimental evidence relates these MMP activities to increased permeability of the blood-brain-barrier (BBB), infiltration of inflammatory cells, and progression of HIV-1 associated dementia (Power, 1993). MMP's-1, -2, -3 and -9 are found at higher mRNA and protein levels in brain tissues of HAD patients (Ghorpade, 2001). Both Collagen type IV and laminin, substrates of MMP-2 and -9, are reduced in these tissues, the former from the basal membrane of the BBB and the latter from neurons (Buttner, 1996; Chen, 1997). Elevated MMP-9 is also found in the cerebral spinal fluid of HIV-infected HAD patients (Conant, 1999). The relationship between MMP-9 and dementia is further emphasized in SIVmac239-infected macaque monkeys, which overexpressed MMP-9 in their microglia, and developed significant loss of cognitive and motor skills as compared with controls (Berman, 1999).

Interestingly, monocyte activation rather than infection appears to be the key mechanism for monocyte migration across the BBB and altered MMP production (Persidsky, 1997). This would imply that therapies would not necessarily need to traverse the BBB in order to be effective. It should be noted, however, that these platinum compounds are likely BBB-penetrable (Landinio, 2001). Tat protein upregulates MMP-9 in monocytes, but can be blocked by tyrosine phosphatase inhibitors, which also block NF-kappaB and prevent IkappaB-alpha degradation (Kumar, 1999). Neurotoxicity induced by Tat proteins can be inhibited by the MMP (-2, -3, -9, -13 and −14) inhibitor prinomastat in murine models (Johnston, 2001). HAD remains the leading cause of morbidity in AIDS.

MMP-2 has been shown to associate directly with caveolin-1 in human endothelial cells, together with the transmembrane metalloproteinase, MT1-MMP and alpha v beta 3 integrin (Puyraimond, 2001; Gálvez, 2004). Both MMP-2 and MMP-9 are increased in a murine caveolin-1 knockout model, contributing to tumor metastasis. Caveolin-1 is considered a suppressor of these proteins (Williams, 2005; Williams 2004).

Example 8

Murine Serum Measures

Data presented in Table 17 compare Rules-Based Medicine, RBM (Austin, Tex.), murine blood plasma markers in a disease challenge model as compared with HK Inhibitor—a platinum(IV) compound—and with reference standards (no drug). Tumor challenge increases inflammatory markers of specific measures. Tumor-bearing mice receiving 5 mg/kg inhibitor twice weekly over 3.5 weeks showed significant reductions in these markers more closely reflecting normal expressions of the reference group. While the reference group was not part of the experimental group for this data, reference measures from RBM support therapeutically functional reductions of inflammatory cytokines.

Both IL-1beta and IL-6 serum levels are significantly reduced by the inhibitor; these two cytokines are required for TH17 T-lymphocyte differentiation in human and murine models (Weaver, 2007) and therefore, anticipated to reduce this cell subset. TH17 subsets produce IL-17, whose overproduction is associated with numerous autoimmune disorders such as multiple sclerosis, rheumatoid arthritis, inflammatory bowel disorder, and others.

TABLE 17

Data Comparing Rules-Based Medicine Murine Blood Plasma Markers In A Disease Challenge Model As Compared With HK Inhibitor And With Reference Standards (no drug)

|  | Disease Challenge Model (n = 4) | Disease Challenge plus Inhibitor (n = 8) | Reference Values No Disease † (n = 5) |
|---|---|---|---|
| IL-1beta (ng/mL) | 0.27 ± 0.15 | 0.19 ± 0.09 | 0.1 ± 0.1 |
| IL-6 (pg/mL) | 30 ± 17 | <14 * | 24 ± 15 |
| IL-10 (pg/mL) | 270 ± 143 | 214 ± 96 | <109** |
| IL-18 (ng/mL) | 1.8 ± 0.3 | 1.2 ± 0.1 | 0.8 ± 0.6 |
| VEGF (pg/mL) | 279 ± 77 | 194 ± 23 | 24 ± 16 |
| VCAM-1 (ng/mL) | 1800 ± 300 | 1400 ± 100 | 1400 ± 200 |
| MMP-9 (ng/mL) | 24 ± 13 | 12 ± 1 | (no data) |
| MIP-1alpha (ng/mL) | 0.19 ± 0.01 | 0.15 ± 0.03 | 0.07 ± 0.04 |
| MIP-3beta (ng/mL) | 0.28 ± 0.09 | 0.17 ± 0.06 | 0.24 ± 0.12 |
| MIP-1gamma (ng/mL) | 23 ± 7 | 9 ± 1 | 14 ± 4 |
| MIP-2 (pg/mL) | 23 ± 8 | 9 ± 3 | 23 ± 17 |
| CD40 (pg/mL) | 214 ± 74 | 107 ± 27 | (no data) |
| CD40 Ligand (pg/mL) | 39 ± 12 | 24 ± 5 | (no data) |
| Eotaxin (pg/mL) | 318 ± 120 | 202 ± 46 | 340 ± 73 |
| Lymphotactin (pg/mL) | 75 ± 16 | 25 ± 12 | 84 ± 46 |
| MCSF (ng/mL) | 4.2 ± 0.5 | 3.3 ± 0.2 | 3.4 ± 0.2 |
| MDC (pg/mL) | 340 ± 44 | 255 ± 33 | 51 ± 14 |
| TIMP-1 (ng/mL) | 3.2 ± 0.9 | 0.9 ± 0.3 | 2.1 ± 1.1 |
| Leptin (ng/mL) | 0.4 ± 0.1 | 1.2 ± 0.7 | 0.7 ± 0.2 |
| GCP-2 (ng/mL) | 6 ± 8 | 3 ± 2 | 5 ± 5 |
| MCP-1 (pg/mL) | 123 ± 44 | 31 ± 6 | 83 ± 58 |
| MCP-3 (pg/mL) | 335 ± 121 | 85 ± 25 | 158 ± 84 |
| MCP-5 (pg/mL) | 101 ± 42 | 40 ± 11 | 60 ± 18 |
| IP-10 (pg/mL) | 160 ± 34 | 62 ± 24 | 62 ± 23 |

* These measures were below the detection limit of 14 pg/mL
**These measures were below the detection limit of 109 pg/mL
† These values are from the Charles River Laboratories for C57/BL adult male mice MCP's:

Important to HIV therapies, reductions in Monocyte Chemoattractant Proteins (MCP)-1, -3 and -5 (of the C—C Chemokines) affect immune cell recruitment and infiltration; human serum MCP-1 (analogous to murine MCP-5) is associated with dementia and markedly a predictor of death (Sevigny, 2007). Monocyte activation, rather than HIV-1 infection, per se, is suggested to be the larger factor in monocyte migration across the BBB (Webster, 2006; Clay, 2007). Both astrocytes and endothelial cells produce MCP-1 in response to lentiviral proteins in humans.

Inducible Protein (IP)-10:

Also known as CXCL10, this cytokine has been studied in HIV patients and shown to correlate with WBCs and plasma RNA from the CSF but not with blood serum measures (Cinque, 2005). IP-10 has been shown to stimulate HIV-1 replication in both monocyte-derived macrophages and peripheral blood lymphocytes; blocking its action is a proposed therapeutic target (Lane, 2003).

Eotaxin:

CCL24/eotaxin-2 may be part of the mechanism of CD4+ lymphocyte activation paracrinally induced by HIV-1 Nef regulatory protein. Nef stimulates monocyte-derived macrophages through STATs and other pathways leading to the production and release of cytokines such as eotaxin-2, activating quiescent CD4+ T-lymphocytes. Antibodies to eotaxin neutralized this stimulatory effect (Fiorucci, 2007).

MDC:

Macrophage-derived chemokine/CCL22 is secreted by dendritic cells and macrophages; it is a chemoattractant for activated T-cells, monocytes, dendritic cells and natural killer cells. Its receptor is CCR4, also used by HIV. Its role in trafficking T-cells may contribute to infiltration of infected cells across the blood-brain barrier. CD16+ monocytes that preferentially differentiate into macrophages may activate resting T cells for productive HIV infection by producing specific CCR4 ligands such as MDC/CCL22 (Ancuta, 2006).

Interleukin-10:

Cytokines such as IL-10, IL-3, TNF-alpha, GM-CSF and TGF-beta associate with more than one immune response subtype; IL-10 participates in both TH2 and TH3 (T-helper lymphocyte) subtypes. Widely produced by T-cells, B-cells and macrophages, it serves to negatively regulate TH1 responses. Increased IL-10 production in IL-2-responsive TH3 cells has been shown to involve STAT5 activation distinct from IL-10 production in IL-2-non-responsive TH2 cells (Tsuji-Takayama, 2007). Other studies conclude that STAT3 mediates anti-inflammatory effects of IL-10 upon macrophages, suggesting a protective role of STAT3 for this cell type (Matsukawa, 2005).

CD40/CD40L:

Also known as CXCL8, CD40 is a CXC chemokine that recruits leukocytes to sites of inflammation and has been demonstrated in neuroinflammatory CNS diseases, including HIV-encephalitis. CD40 is a protein on the surface of microglia which associates with CD40Ligand; their interaction leads to chemokine expressions that recruit inflammatory cells into the CNS (D'Aversa, 2007).

DEFINITIONS AND METHODS

As used herein, alkyl means straight or branched chain, saturated or mono- or polyunsaturated hydrocarbon groups having from 1 to 20 carbon atoms, and C1-X alkyl means straight or branched chain alkyl groups containing from one up to X carbon atoms. For example, C1-6 alkyl means straight or branched chain alkyl groups containing from one up to 6 carbon atoms. Alkoxy means an alkyl-O-group in which the alkyl group is as previously described. Cycloalkyl includes a nonaromatic monocyclic or multicyclic ring system, including fused and spiro rings, of from about three to about 10 carbon atoms. A cyclic alkyl may optionally be partially unsaturated. Cycloalkoxy means a cycloalkyl-O-group in which cycloalkyl is as defined herein. Aryl means an aromatic monocyclic or multicyclic carbocyclic ring system, including fused and spiro rings, containing from about six to about 14 carbon atoms. Aryloxy means an aryl-O-group in which the aryl group is as described herein. Alkylcarbonyl means a RC(O)-group, where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group, where R is a cycloalkyl group as previously described.

Heteroalkyl means a straight or branched chain having from one to 20 carbon atoms and one or more heteroatoms selected from nitrogen, oxygen, or sulfur, wherein the nitrogen and sulfur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulfur atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulfur and wherein an N atom may be in the form of an N-oxide. Arylcarbonyl means an aryl-CO-group in which the aryl group is as described herein. Heteroarylcarbonyl means a heteroaryl-CO-group in which the heteroaryl group is as described herein and heterocycloalkylcarbonyl means a heterocycloalkyl-CO-group in which the heterocycloalkyl group is as described herein. Aryloxycarbonyl means an ROC(O)— group, where R is an aryl group as previously described. Heteroaryloxycarbonyl means an ROC(O)— group, where R is a heteroaryl group as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, thiazolyl, pyrazolyl, pyridyl, indolyl, quinolinyl, isoquinolinyl, benzoquinolinyl, carbazolyl, and diazaphenanthrenyl.

As used herein, halogen means the elements fluorine (F), chlorine (Cl), bromine (Br), and iodine (I).

The term pharmaceutically acceptable salts means salts of the platinum compounds of the invention which are prepared with acids or bases, depending on the particular substituents present on the subject compounds described herein. Examples of a pharmaceutically acceptable base addition salts include sodium, potassium, calcium, ammonium, or magnesium salt. Examples of pharmaceutically acceptable acid addition salts include hydrochloric, hydrobromic, nitric, phosphoric, carbonic, sulfuric, and organic acids like acetic, propionic, benzoic, succinic, fumaric, mandelic, oxalic, citric, tartaric, maleic, and the like. Pharmaceutically acceptable salts of platinum compounds of the invention can be prepared using conventional techniques.

It will be appreciated by those skilled in the art that certain of the platinum compounds of the invention may contain one or more asymmetrically substituted carbon atoms which can give rise to stereoisomers. All such stereoisomers, including enantiomers, and diastereoisomers and mixtures, including racemic mixtures thereof, are contemplated within the scope of the present invention. Examples include: (1) FX-101, which is the trans-isomer of diaminotrichloronitroplatinum (IV); CPA-7, which is the cis-isomer of diaminotrichloronitroplatinum(IV); and NAD which is the cis-isomer of diaminodichloronitronicotinamideplatinum (IV).

Platinum compounds of the present invention have been shown to associate with caveolin proteins, lipid rafts, and/or caveolae. These associations result in modulation of cellular functions known to be controlled or associated with these important organelles normally present within cellular membranes. Both in vitro and in vivo studies have confirmed therapeutic value for numerous diseases and disorders while exhibiting low to no apparent complications of toxicity. These small molecules are advantageous for transient and intermittent modulation of disease-associated cellular functions for both local and systemic effects such that recovery of healthy functions is facilitated.

Methods of the invention comprise modulating functions or structures associated with caveolae, lipid rafts, and/or caveolin proteins. These are established therapeutic targets for a wide range of diseases and disorders due to their ubiquitous presence across cell types, interaction with cell receptors, transport functions, cholesterol homeostasis and in recruitment and regulation of cell signaling and transcription (Thomas 2008; Frank, 2006; Cohen, 2004; Williams, 2004; Liu, 2002; Smart, 1999; Okamoto, 1998). Thus, implications for caveolar or lipid raft involvement in numerous diseases include diabetes, diabetic retinopathy, cancer, cardiovascular diseases, artherosclerosis, pulmonary fibrosis, degenerative muscle diseases, neuronal diseases, autoimmune diseases, and others (Benarroch, 2007; Frank, 2007; Michel, 2007; Silva, 2007; Xu, 2007; Frank 2004).

In one embodiment, the method comprises contacting a cell with a platinum compound of the invention. In one embodiment, the cell is a tumor cell, cancer cell, viral-infected cell, immune cell, liver cell, heart cell, pancreatic cell, epithelial cell, endothelial cell, hematopoetic cell, stem cell, glial cell, neuronal cell, retinal pigment endothelial cell (Mora, 2006), adipocyte, osteoblast (Solomon, 2000) or a transformed cell. In another embodiment, the cell can be bacterial, parasitic, or viral. The cell can be a cell from a mammal, including human, monkey, chimpanzee, ape, dog, cat, cow, pig, and horse.

Lipid rafts are organized structures of lipids found within the bilayer membrane of a cell. These provide heterogeneity for the aggregation of proteins comprising receptors or signaling complexes. The functional significance of lipid rafts is their mandatory requirement for successful functionalities of many associated lipids and proteins.

Caveolae are defined as pleomorphic assemblies of sphingolipids, phospholipids, cholesterol, various glycosylphosphatidylinositol (GPI)-anchored molecules and usually contain caveolin protein. These may be located in cell membranes, intracellular vacuoles of the cytosol, the endoplasmic reticulum, mitochondria, Golgi apparatus, or other cellular organelles (McMahon, 2006), or even secreted into the extracellular matrix (Sawada, 2007). They may be morphologically identified as plasma membrane invaginations, generally appearing as 50-100 nm flasks, although may also be grapelike clusters, tubular structures or other shapes (Anderson, 1998). Caveolin proteins are the major structural proteins of caveolae, transport proteins of cholesterol and scaffolding proteins of signaling molecules. Caveolae are present in skeletal muscle cells and keratinocytes, the lumen of secretory vesicles (such as serous cells of pancreas, funic stomach and salivary gland), epithelial cells (especially of the lung), adipocytes, hepatocytes, in nervous tissue, white blood cells, osteoblasts, retinal epithelial cells and others. Caveolae may be known as: detergent-insoluble glycolipid-rich domains; detergent-resistant membranes (DRMs), or fragments; Triton-insoluble domains; cholesterol-enriched liquid-ordered domains or membrane microdomains (CEMM); detergent-insoluble glycolipid-rich membranes (DIGs); cholesterolsphingolipid rafts; glycolipid-enriched membranes (GEMs); detergent-resistant membranes; caveolin-enriched membranes; low-density Triton-insoluble domains; or caveola-like or caveola-related domains (deficient of caveolin protein).

Platinum compounds of the invention can be delivered to a cell either through direct contact with the cell or via a carrier means. Carrier means for delivering compositions to cells are known in the art and include, for example, a liposome or moiety or nanomaterial such as carbon nanoparticles. Another means for delivery of platinum compounds of the invention to a cell comprises attaching the platinum compound to a protein, sugar or nucleic acid that is targeted for delivery to the target cell. Platinum compounds can be incorporated into polymers, examples of which include poly (D-L lactide-co-glycolide) polymer for intracranial tumors; poly [bis(p-carboxyphenoxy) propane:sebacic acid] in a 20:80 molar ratio (as used in GLIADEL); chondroitin; chitin; and chitosan. Of specific relevance are targeting methods suitable to cell membranes (nonpolar glycolipids, receptors, e.g.) of specific cell types related to specific therapeutic needs.

The subject invention also concerns multiple methods for preventing or treating oncological disorders in a patient: reducing tumor growth, inhibiting cellular transformation, inhibiting metastasis, inhibiting angiogenesis, activating apoptotic pathways and/or activating both innate and immune responses. In one embodiment, an effective amount of a platinum compound of the present invention is administered to a patient having an oncological disorder and who is in need of treatment therefor. Methods of the invention can optionally include identifying a patient who is or may be in need of treatment for an oncological disorder. The patient can be a human or other mammal, such as a primate (monkey, chimpanzee, ape, etc.), dog, cat, cow, pig, or horse, or other animals having an oncological disorder. Means for administering and formulating platinum compounds for administration to a patient are known in the art, examples of which are described herein. Oncological disorders include cancers and/or tumors of the bone, breast, kidney, mouth, larynx, esophagus, stomach, testis, cervix, head, neck, colon, ovary, lung, bladder, skin (e.g., melanoma), liver, muscle, pancreas, prostate, eye (e.g., retinoblastoma), blood cells (including stem cells), and brain.

For the treatment of oncological disorders, the platinum compounds of this invention can be administered to a patient in need of treatment in combination with other antitumor or anticancer substances; or with radiation, electroporation, radio waves, immunotherapy, photodynamic therapy; or with surgical treatment to remove a tumor. These other substances or treatments may be given at the same as or at different times from the platinum compounds of this invention. For example, the platinum compounds of the present invention can be used in combination with mitotic inhibitors such as taxol or vinblastine, alkylating agents such as cyclophosamide or ifosfamide, antimetabolites such as 5-fluorouracil or hydroxyurea, DNA interchelators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr virus (EBV), Herpes Papillomavirus (HPV) and Hepatitus Virus C(HPVC) are each associated with a number of mammalian malignancies. The platinum compounds of the subject invention can be used alone or in combination with another anticancer and/or antiviral agent, such as ganciclovir, azidothymidine (AZT), lamivudine (3TC), maraviroc, raltegravir, etc., to treat patients infected with a virus that can cause cellular transformation and/or to treat patients having a tumor or cancer that is associated with the presence of viral genome in the cells. The platinum compounds of the subject invention can also be used in combination with viral-based treatments of oncologic disease.

Some platinum compounds of the present invention have also been shown to inhibit Signal Transducers and Activators of Transcription (STAT) activity (Turkson, 2004). It is anticipated that such platinum compounds of the invention may indirectly disrupt STAT activity through lipid rafts, the caveolin scaffolding domain—either directly, or through inactivation of tyrosine kinases modulated through caveolin proteins—or through transport functions. Inconsistency between STAT activity and platinum inhibition in some cell lines further implies another point of control. Other upstream regulators of STAT activation, such as RAGE (receptor for advanced glycation end products), are known to be modulated by caveolin-1 (Reddy, 2006), also explaining this observation. Since trafficking of STAT proteins is known to include lipid rafts in the "raft-STAT-signaling hypothesis" (Sehgal, 2002), the effect may also be owed to platinum associating with caveolin proteins found within lipid rafts. Caveolin-1 deficient mice exhibit constitutively activated STAT3 proteins as well as upregulation of cyclin D1 and D3 proteins (Jasmin, 2006).

Platinum compounds have been shown to reduce tumor cell growth and metastasis in vitro and in vivo (Turkson 2004; Kortylewski 2005), although efficacies depend upon cell type. Complicating toxicities of platinum compounds usually affect kidney, liver, and neuronal cells. Compounds of the current invention are advantageous for selectivity in cells characterized by loss or reduction of lipid raft-related or caveolae-related functionalities, often correlating with reduced caveolin expression and/or activation in these cells. Thus, compounds of the invention have been shown to enhance caveolar and lipid raft functions and are useful for cancers whereby increasing caveolin activity inhibits tumor growth, transformation or metastasis.

Relatively low effective therapeutic concentrations and very low toxicities as compared with other platinum compounds provide distinct advantages. Furthermore, biological reduction of certain compounds of the invention leading to transplatinum(II) compounds exhibit much reduced toxicities as compared with cisplatinum(II) derivatives; these trans isomers have also demonstrated greater potential as caveolae/lipid raft effectors as compared with corresponding cis isomers. Platinum compounds of the invention can be tested for activity in suitable assays, such as MTT or TUNEL assays, cytokine/chemokine production/sensitivity assays, receptor expression and functionality assays, etc. Since immune cells and epithelial cells may also contribute to tumor growth and metastasis, in vitro assays may not fully reflect in vivo therapeutic capacities of these compounds.

The subject invention also concerns methods for preventing or treating bacterial, viral, or prion infections of a patient using a platinum compound of the invention, including the host immune responses to infections. In one embodiment, an effective amount of a platinum compound of the invention is administered to a patient to prevent or treat a bacterial or viral infection. Methods of the invention can optionally include identifying a patient who is or may be in need of treatment of a bacterial, viral, or prion infection. The patient can be a human or other mammal, such as a primate (monkey, chimpanzee, ape, etc.), dog, cat, cow, pig, or horse, or other animal infected with a bacteria or virus. Bacterial infections that can be treated according to the present invention include at least those from *Staphylococcus, Streptococcus, Salmonella, Bacillus, Clostridium, Pseudomonas, Neisseria, Mycobacterium*, and *Yersinia*, inclusive of resistant strains. Viral infections that can be treated according to the present invention include, but are not limited to, those associated with human immunodeficiency virus (Hofstetter, 2007), feline immunodeficiency virus (FIV), human T-cell leukemia virus (HTLV), Papillomavirus (e.g, human papilloma virus (HPV)), Polyomavirus (e.g., SV40, BK virus, DAR virus), orthopoxvirus (e.g., variola major virus (smallpox virus)), Epstein Barr Virus (EBV), herpes simplex virus (HSV), hepatitis virus, Rhabdovirus (e.g., Ebola virus) and cytomegalovirus (CMV). Platinum compositions of the present invention can also be used to treat bacterial, viral, or prion diseases in the presence of other therapies such as antimicrobials or antivirals. It is contemplated that these compounds interfere with pathogen-related (i.e., including proteins and toxins of pathogenic origins) hijacking of lipid rafts (Taylor, 2006; Russelakis-Carneiro, 2004), caveolar mechanisms, host cell receptor expressions and functions, transcription and apoptotic pathways such that direct pathogen inhibition together with indirect host innate and adaptive immune responses are enabled.

The subject invention also concerns methods for preventing or treating diabetes mellitus in a patient. In one embodiment, an effective amount of a platinum compound of the present invention is administered to a patient having a diabetic disorder and who is in need of treatment thereof. Methods of the invention can optionally include identifying a patient who is or may be in need of treatment for a diabetic disorder. The patient can be a human or other mammal, such as a primate (monkey, chimpanzee, ape, etc.), dog, cat, cow, pig, or horse, or other animals having a diabetic disorder. Means for administering and formulating platinum compounds for administration to a patient are known in the art, examples of which are described herein. Diabetic disorders include diabetes mellitus, type I diabetes, type II diabetes, prediabetic conditions, diabetic retinopathy, diabetic nephropathy, acute diabetic complications (hypoglycemia, ketoacidosis, nonketotic hyperosmolar coma), long-term diabetic complications (cardiovascular disease, doubled risk, chronic renal failure, retinal damage, nerve damage and microvascular damage). It is contemplated that platinum compounds of the invention downregulate aggravating chemokines, cytokines and vascular adhesion molecules associated with the onset and progression of diabetic conditions; reduce autoimmune responses; as well as modulate the insulin receptor known to interface with caveolae and caveolin proteins.

Platinum compounds of the subject invention can also be used to treat patients for autoimmune diseases and disorders. In one embodiment, the patient is administered a therapeutically effective amount of a platinum compound of the present invention. Methods of the invention can optionally include identifying a patient who is or may be in need of treatment of an autoimmune disorder. The patient can be a human or other mammal, such as a primate (monkey, chimpanzee, ape, etc.), dog, cat, cow, pig, or horse, or other animal infected with a parasitic organism. Disease conditions that can be treated according to the present invention include, but are not limited to: arthritis, multiple sclerosis, allergies, asthma, psoriasis, lupus erythematosus, irritable bowel syndrome (or inflammatory bowel disease, IBD), diabetes, Crohn's disease, Alzheimer's disease, Sjögren's syndrome, AIDS, and Parkinson's disease (Wolk, 2007; Jury, 2007; Tzartos, 2007; Toh, 2007). It is contemplated that platinum compounds of the invention inhibit the development and cytokine productions associated with CD4+ T-helper lymphocyte population subsets, designated TH17, which are known to be responsible for many autoimmune disorders including those related to pathogenic origins (Ouyang, 2008). Furthermore, it is contemplated that platinum compounds of the invention modulate the Transforming Growth Factor Receptor (TGFR), containing a caveolin-1 scaffolding domain, and critical to T-helper Lymphocyte cell subset (TH17) development and activity, including production of inflammatory cytokines TGFbeta (Transforming Growth Factor beta) together with Interleukins (IL)-17, IL-21, IL-22, and IL-6.

Platinum compounds of the subject invention can also be used as an adjuvant to enhance antigen presenting immune responses in a patient or to develop a vaccine in vitro, in vivo, or ex vivo. In one embodiment, a patient is administered a therapeutically effective amount of a platinum compound of the present invention to activate immune responses together with a vaccine. In another embodiment, an effective amount of a platinum compound is introduced to an animal, such as a rabbit, together with an antigen (which may be a protein, peptide fragment, living or attenuated cell, virion, or sugar) to elicit the production of antibodies. In another embodiment, an effective amount of a platinum compound is introduced ex vivo to activate antigen-presentation responses for a patient in need of immune therapy. In another embodiment, a patient is administered a therapeutically effective amount of a platinum compound to stimulate immune responses in the presence of a pathogen. Methods of the invention can optionally include identifying a patient who is or may be in need of vaccine therapy. The patient can be a human or other mammal, such as a primate (monkey, chimpanzee, ape, etc.), dog, cat, cow, pig, or horse, or other animal. Platinum compounds of the invention are contemplated to enhance lipid raft/caveolar assemblies associated with the T-cell antigen receptor for T-cells or the membrane-bound immunoglobulin molecule on B-cells; enable major histocompatability complex class I complexes; facilitate signaling through cellular receptors; enhance maturity of immune cells; and support endocytotic pathways for antigen-presentation.

Platinum compounds of the subject invention can also be used to treat patients infected with a parasitic organism, including the host immune responses to infection. In one embodiment, the patient is administered a therapeutically effective amount of a platinum compound of the present invention. Methods of the invention can optionally include identifying a patient who is or may be in need of treatment of a parasitic infection. The patient can be a human or other mammal, such as a primate (monkey, chimpanzee, ape, etc.), dog, cat, cow, pig, or horse, or other animal infected with a parasitic organism. Disease conditions that can be treated according to the present invention include, but are not limited to: *leishmania*, toxoplasmosis, schistosomiasis, trypanosomiasis, *pneumocystis*, malaria, and trichinosis. Parasitic organisms that can cause disease conditions treatable according to the present invention include, but are not limited to, *Leishmania, Toxoplasma, Schistosoma, Plasmodium*, and

*Trypanosoma*. The subject invention can also be used to treat gastro-intestinal disorders caused by parasitic organisms such as: *Entamoeba, Giardia, Trichomonas*, and nematodes such as *Ascaris, Trichuris, Enterobius, Necator, Ancylostoma, Strongyloides*, and *Trichinella*. In another embodiment, a platinum compound of the present invention can be administered to patients prophylactically, wherein an uninfected patient is traveling to or will be present in an area where parasitic disease is prevalent or poses a risk to the patient. Accordingly, the patient can be treated with a composition of the present invention prior to the patient's exposure to or presence in the area where parasitic disease is prevalent or poses a risk and/or prior to infection with the parasitic organism.

Platinum compounds of the subject invention can also be used to treat patients for cardiovascular diseases and disorders. In one embodiment, the patient is administered a therapeutically effective amount of a platinum compound of the present invention. Methods of the invention can optionally include identifying a patient who is or may be in need of treatment of a cardiovascular disorder. The patient can be a human or other mammal, such as a primate (monkey, chimpanzee, ape, etc.), dog, cat, cow, pig, or horse, or other animal infected with a parasitic organism. Disease conditions that can be treated according to the present invention include, but are not limited to: coronary artery disease and other atherosclerotic vascular diseases (thrombosis of other major vessels, ischaemic renal disease or peripheral arterial disease—also called arthritis), aortic aneurysm, hypertension, ventricular septal perforation or cardiac rupture in acute myocardial infarction, coronary heart disease, ischemic stroke, atherosclerosis, aneurysm, cerebrovascular disease, hypertension and rheumatic heart disease. It is contemplated that platinum compounds of this invention are useful for treatment of cardiovascular disorders through modulation of: inflammatory cell infiltration; expression and activation of cell surface receptors; calcium and cholesterol homeostasis; nitric oxide production as well as cytokine and chemokine productions related to cardiovascular disorders. Cytokines, chemokines, and other soluble factors modulated through caveolae related to cardiovascular diseases include: Monocyte Chemoattractant Proteins (MCP's), Interleukin-1B (IL-1B), Interleukin-6 (IL-6), Interleukin-10 (IL-10), eotaxin, nitric oxide, calcium ions, Vascular Cell Adhesion Molecule-1 (VCAM-1) and Matrix Metalloproteinase-2 and -9 (MMP-2 and -9). Both endothelial nitric oxide synthase (eNOS) and inducible nitric oxide synthase (iNOS) are known to interact with caveolae (Ichinose, 2007).

Platinum compounds of the present invention can also be used to treat biological products in vitro that are contaminated with or suspected of being contaminated with a virus on a bacterial or parasitic organism. Biological products that can be treated with a platinum compounds of the present invention include, but are not limited to, whole blood, fractionated blood, plasma, serum, whole organs, or parts of organs, and cells, including blood cells, muscle cells, skin cells, and neuronal cells, and products derived from cells. Products derived from cells that can be treated with a platinum compound of the present invention include, but are not limited to: interferons, interleukins, blood clotting factors such as factor VIII, IX, X, and the like, insulin, polyclonal and monoclonal antibodies, growth factors, cytokines, and other products. Treatment of biological products comprises contacting the product for an effective amount of time and with an effective amount of a platinum compound of the present invention. If necessary, the biological product can be subsequently washed, preferably with a suitable sterile wash solution such as phosphate buffered saline, to remove the platinum compound that was used to treat the product.

Therapeutic application of the subject platinum compounds, and compositions containing them, can be accomplished by any suitable therapeutic method and technique presently or prospectively known to those skilled in the art. The subject platinum compounds can be administered by any suitable route known in the art including, for example, oral, nasal (e.g., via aerosol inhalent), rectal, ex vivo (reintroduction of treated tissues), and parenteral routes of administration. As used herein, the term parenteral includes topical, subdermal (e.g., as in an implant), subcutaneous, intradermal, intravenous, intramuscular, intraperitoneal, and intrasternal administration, such as by injection. Administration of the subject platinum compounds of the invention can be continuous or at distinct intervals as can be readily determined by a person skilled in the art.

Platinum compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that a bioeffective amount of the platinum compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, aerosol particle, and sprays. The preferred form depends on the intended mode of administration and therapeutic application. The compositions also preferably include conventional pharmaceutically acceptable carriers and diluents which are known to those skilled in the art. Examples of carriers or diluents for use with the subject platinum compounds include ethanol, ethyl acetate, dimethyl sulfoxide, glycerol, alumina, starch, and equivalent carriers and diluents. To provide for the administration of such dosages for the desired therapeutic treatment, pharmaceutical compositions of the invention will advantageously comprise between about 0.1% and 99%, and especially, 1 and 15% by weight of the total of one or more of the subject platinum compounds based on the weight of the total composition including carrier or diluent.

The platinum compounds of the subject invention can also be administered utilizing liposome technology, antibody-conjugation, peptide-conjugation, nanotechnology (such as carbon nanotubes, gold nanospheres, or nanoslow-release capsules), polymeric sugars, electroporation, implantable pumps, and biodegradable containers. Certain of these delivery methods can, advantageously, provide a uniform dosage over an extended period of time while others provide immediate and/or local targeting. The platinum compounds of the present invention can also be administered in their salt derivative forms or crystalline forms known to those of ordinary skill in the art.

The subject invention also concerns a packaged dosage formulation comprising in one or more containers at least one platinum compound of the subject invention formulated in a pharmaceutically acceptable dosage.

Synthesis of Platinum Compounds

Using 0.300 grams of Cisplatin (0.00100 moles, FW=300.1) or transplatin, 150 mL of ultra deionized water are added to a 250-mL Erlenmeyer flask. Additionally, cosolvents such as hexane, dichlorethane or other organic solvents can be added as well. Cis-diammineoplatinum(II) dichloride (cisplatin) can be purchased at 99.9% purity from Sigma-Aldrich (Product No. 4394). Trans-platinum (II) diammine dichloride (transplatin) can be purchased from Sigma-Aldrich (Product No. 1525). The choice of a sixth ligand includes the availability of a nitrogen, sulfur, phosphorous or oxygen atom in the chemical structure providing a Lewis base for bonding to the oxidized Pt. Other ligands are possible with other metals, halides or through chelation or interaction with pi molecular orbitals. One mole of the chosen ligand per mole of cisplatin should be weighed and added to the mixture. Silver nitrate can be added to remove chloride ligands and replace these with other ligands, since silver chloride precipitates are easily separated by filtration. Dichloroethane, e.g., provides solubility for organic ligands of hydrophobic nature and various cosolvents will alter the final crystalline structure and co-crystal structures possible in the final product. A magnetic stir bar is placed in the mixture and the flask placed on a magnetic stir plate in a chemical fume hood. An organic nitrite such as ethylnitrite or butylnitrite; or an inorganic nitrate such as potassium nitrite can be added to oxidize the platinum(II) to platinum(IV). A blue color is noted to indicate formation of the nitrosyl intermediate; variations in hue and duration of this color have been observed. Organic nitrites simplify separation of the final product, since the remaining organic solvent (e.g., ethane for ethylnitrite) can be boiled or evaporated away. The flask should be covered in aluminum foil to prevent light exposure and left to stir overnight. The mixture requires air for complete oxidation, so should not be tightly covered. Continued oxidation with air can be accelerated using air blown through a trap into the Erlenmeyer, over the liquids. The solvents will evaporate in about two days, leaving a yellow (or other color-depending on choice of ligands) precipitate, which is the product.

The precipitate can be purified via recrystallization in methanol, diethyl ether, acetone, or other suitable solvent. Alternatively, the product can be purified on silica-type columns or using HPLC.

All patents, patent applications, provisional applications, and publications referred to or cited herein are incorporated by reference in their entirety, including all figures and tables, to the extent they are not inconsistent with the explicit teachings of this specification. Among those intended to be incorporated by reference are: US Patent Applications 2005/0288365, 2005/0080131, 2005/0074502, and 2005/0288365, and PCT Applications WO2007/006019, 2005/023824, and 2005/016946.

Methods of Use of a Composition of the Present Invention

A composition of the present invention has a plurality of methods of use, including, but not intended to be limited to:

A method of treating an oncological disorder in a patient, wherein the transformed or malignant cells are characterized by dysregulation of signaling proteins, transduction proteins, membrane receptors, apoptotic pathways or cellular transport normally modulated through caveolae and/or lipid rafts, comprising administering an effective amount of platinum(IV) compound to the patient.

A method of treating or preventing tumor immune evasion responses in a patient, comprising administering an effective amount of a platinum(IV) compound to activate innate and/or adaptive immune responses affected through lipid rafts, caveolae, and/or caveolin proteins in white blood cells, including dendritic cells, macrophages, stem cells, mast cells, lymphocytes, and/or monocytes, either in vivo or ex vivo.

A method of inhibiting, preventing, or treating cancer metastasis by administering an effective amount of a platinum(IV) compound to a patient to modulate caveolar functions or structure related to modulation of Matrix Metalloproteinases (such as MMP-2 or MMP-9), Vascular Endothelial Growth Factor (VEGF), RhoC GTPases (actin cytoskeleton rearrangement), Interleukin-6 (IL-6) or anchorage-independent growth (through inhibition of Erk/PI3kinase and Rac).

A method of inhibiting or preventing cancer or tumor development associated with viral cell transformations in a patient comprising administering an effective amount of a platinum(IV) compound prophylactically, such as caused by Human Immunodeficiency Virus-1 in Karposi's Sarcoma; Epstein-Barr Virus in Burkitt's Lymphoma; Hepatitis B or Hepatitis C Viruses in liver cancer; Human Herpes Virus-8 and Simian Virus 40 in lymphomas; Human Papillomavirus (HPV) in cervical cancer, etc.

A method of treatment for cardiovascular diseases, including but not limited to, myocardial infarction, ischemic stroke, atherosclerosis, aneurysm, peripheral arterial disease, and/or coronary artery disease, in a patient comprising the administration of an effective amount of a platinum(IV) compound for the modulation of caveolae function or structure related to cardiovascular diseases. Cytokines, chemokines and other soluble factors modulated through caveolae related to cardiovascular diseases include: Monocyte Chemoattractant Proteins (MCP's), Interleukin-1B (IL-1B), Interleukin-6 (IL-6), Interleukin-10 (IL-10), eotaxin, nitric oxide, calcium ions, Vascular Cell Adhesion Molecule-1 (VCAM-1) and Matrix Metalloproteinase-2 and -9 (MMP-2 and -9).

A method of treatment for multiple sclerosis whereby an effective amount of a platinum(IV) compound is administered to a patient to modulate caveolar structure or functions such as those involving Interleukin-6 (IL-6), CD40, CD40 Ligand (CD40L, a.k.a. CD154, TNFSF5, TRAP or gp39), Macrophage Inflammatory Protein-2 (MIP-2, CXLC2) or Interleukin-18 (IL-18).

A method of use comprising the administration of an effective amount of platinum(IV) compound to a patient for the treatment of muscular dystrophy, including but not limited to limb-girdle muscular dystrophy, rippling muscle disease or Duchenne muscular dystrophy, whereby caveolar structure or function is modulated.

A method of use comprising the administration of an effective amount of platinum(IV) compound to a patient for the treatment of rheumatoid arthritis, whereby the platinum(IV) compound interacts with caveolae to reduce inflammatory factors such as Matrix Metalloproteinases (MMP-2, MMP-9), Monocyte Chemoattractant Protein-1 (MCP-1), Transforming Growth Factor beta (TGFbeta) or Interleukin-17 (IL-17).

A method of use comprising the administration of an effective amount of platinum(IV) compound to a patient for the prevention, treatment, or symptoms associated with infectious diseases of viral, parasitic, bacterial, or prion origin, whereby the microbe utilizes caveolae for infection, reproduction, activation, assembly or transport of the microbe, or for the manifestation of disease symptoms through caveolar-mediated cytokine signaling and reception.

A method of use whereby an effective amount of a platinum(IV) compound is administered to a patient alone or in combination with another therapeutic drug whereby drug resistance mechanisms are reduced, such as those involved in Multidrug Resistance (MDR) or upregulation of p53 protein.

A method of use comprising administering an effective amount of a platinum(IV) compound to reduce myelosuppression in a patient, administered either alone or in combination therapy.

A method of use comprising administering an effective amount of a platinum(IV) compound to regulate proteins or receptors associated with caveolin or the caveolin scaffolding domain. Examples of proteins that have been identified to interact with caveolin-1 proteins through the scaffolding domain contain one of the sequences, *xxxx*xx* or *x*xxxx* (where *=an aromatic residue—tryptophan, phenylalanine, or tyrosine and x=any other residue). Such proteins known to associate through caveolin or the caveolin scaffolding domain include, but are not limited to: G proteins; Src family Tyrosine Kinase (s-Src/Fyn and Lyn); Rous Sarcoma kinase (Src); Heat Shock Protein 56 (HSP56); Endothelial Nitric Oxide Synthase (eNOS); Neuronal Nitric Oxide Synthase (nNOS); Tyrosine Kinase A (TrkA); Protein Kinase C(PKC); Signal Transducers and Activators of Transcription Proteins (STATs); Mitogen-Activating Protein Kinase Extracellular signal-Regulated Kinase (MAPK/ERK); Protein Kinase A (PKA); as well as receptors Endothelial Growth Factor Receptor (EGFR); Platelet Derived Growth Factor Receptor (PDGFR); p75 Nerve Growth Factor Receptor (NGFR); Transforming Growth Factor Receptor (TGFR); Estrogen Receptor (ER); Androgen Receptor (AR); and Insulin Receptor (IR). Caveolin-1 may categorically inhibit kinases since the scaffolding binding motif is contained within a highly conserved subdomain IX of both tyrosine and serine/threonine kinases.

A method of use whereby an effective amount of a platinum(IV) compound is administered to treat or prevent diabetes in a patient by reducing conditions associated with diabetes such as regulation of Monocyte Chemoattractant Protein-1 (MCP-1), Inflammatory Protein-10 (IP-10), Insulin production or Insulin Receptor function.

A method of use comprising the use of a platinum(IV) compound in a patient for the prevention or treatment of HIV-, SIV-, or FIV-associated dementia (HAD), whereby modulation of caveolar function reduces cytokines, chemokines or membrane receptors such as Matrix Metalloproteinases-2 or -9 (MMP-2, MMP-9), Monocyte Chemoattractant Proteins (MCP's), Interleukin-6 (IL-6), Inducible Protein-10 (IP-10).

A method of use whereby an effective amount of a platinum(IV) compound is administered to a patient to reduce cell migration into the central nervous system associated with leakage of cells across a compromised blood-brain barrier.

A method of use comprising administering an effective amount of a platinum(IV) compound to a patient to inhibit, treat, or prevent the infection of viruses, prions, viral proteins, toxins, or bacteria through caveolae or lipid rafts or by association with caveolin proteins.

A method of use comprising administering an effective therapeutic amount of a platinum(IV) compound to prevent or inhibit the assembly or conformational change of virion or prion particles associated with caveolae, lipid rafts, and/or caveolin proteins.

A method of use comprising the administration of an effective amount of a platinum(IV) compound for the regulation of lipids that associate with caveolae. Such lipids include, but are not limited to: cholesterol, fatty acids, GM1 ganglioside, and GD3 ganglioside.

A method of use as a vaccine adjuvant comprising administering an effective amount of a platinum(IV) compound either in vivo, in vitro, or ex vivo in conjunction with an antigen in order to enhance antigen presentation of the adaptive immune response system in the production of antibodies or vaccines.

A method of use comprising administering an effective amount of a platinum(IV) compound to a patient in the prevention or treatment of autoimmune diseases, whereby the platinum(IV) compound interacts with caveolae, lipid rafts, and/or caveolin proteins to modulate inflammatory cytokines and/or cell receptors such as Transforming Growth Factor beta (TGFbeta), Interleukin-6 (IL-6), or Interleukin-17.

A method of use comprising the administration of an effective amount of a platinum(IV) compound to a patient to prevent or inhibit the development of AIDS (Auto-Immune Deficiency Syndrome) associated with cytokine dysregulation such as Interleukin-6 (IL-6), Macrophage Inflammatory Protein alpha(MIP-1alpha), Macrophage Inflammatory Protein beta (MIP-1 beta), Interleukin-1 beta (IL-1 beta), Interleukin-6 (IL-6), Interleukin-10 (IL-10) Tumor Necrosis Factor alpha (TNF-alpha), Nuclear Factor kappa beta (NF-kappaB), Inflammatory Protein-10 (IP-10), Interferon gamma (IFN gamma), Matrix Metalloproteinases (MMPs) and/or Vascular Endothelial Growth Factor (VEGF).

A method of use comprising the administration of an effective amount of a platinum(IV) compound to a patient in the prevention or treatment of Retinitis Pigmentosa.

A method of preventing or treating opportunistic infections in a patient under immune-suppressed conditions comprising administration of a therapeutic amount of a platinum(IV) compound to prevent microbial endocytosis through caveolae.

A method of use comprising the administration of an effective amount of a platinum(IV) compound to a patient for the treatment of symptoms associated with asthma.

A method of use comprising the administration of an effective amount of a platinum(IV) compound to a patient for the treatment of symptoms associated with Alzheimers.

A method of use comprising the administration of an effective amount of a platinum(IV) compound to a patient for the treatment of endometriosis.

A method of use comprising the administration of an effective amount of a platinum(IV) compound to a patient for the treatment of conditions associated with Lyme neuroborreliosis.

A method of use comprising the administration of an effective amount of a platinum(IV) compound to a patient for the treatment of conditions associated with Irritable Bowel Syndrome.

A method of use comprising the administration of an effective amount of a platinum(IV) compound in vivo, ex vivo, or in vitro for modulating stem cell activities through interaction with lipid rafts, caveolae, and/or caveolin proteins.

A method of use comprising the use of a platinum(IV) compound with a cell to assess caveolar function, activity, or structure, or to assess any of the associated caveolar protein isoforms, including those of caveolin-1, caveolin-2, or caveolin-3, or those proteins having a caveolin-scaffolding domain sequence identified by either *xxxx*xx* or *x*xxxx* (where *=an aromatic residue—tryptophan, phenylalanine or tyrosine and x=any other residue).

A method of use comprising the use of an effective amount of platinum(IV) compound to facilitate regeneration of liver tissue or in liver transplantation.

A method of use comprising the administration of an effective amount of a platinum(IV) compound to a patient in vivo or ex vivo to inhibit the development of TH17 Thymus lymphocytes and/or the production of inflammatory cytokines associated with this cell subtype such as Interleukin-17 (IL-17), Interleukin-6 (IL-6), or Interleukin-22 (IL-22).

A method of use comprising the administration of an effective amount of a platinum(IV) compound to a patient for the treatment of conditions associated with optical diseases or disorders, including diabetic retinopathy.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the compositions and methods illustrated and described herein are by way of example, and the scope of the invention is not limited to the exact details of structure, synthesis, and use.

Having now described the invention, the operation and use of preferred embodiments thereof, and the advantageous new and useful results obtained thereby, the new and useful constructions, and reasonable equivalents thereof obvious to those skilled in the art, are set forth in the appended claims.

BIBLIOGRAPHY

Afzali, B., G. Lombardi, et al. (2007). "The role of T helper 17 (Th17) and regulatory T cells (Treg) in human organ transplantation and autoimmune disease." *Clin Exp Immunol* 148(1): 32-46.

Ancuta, P., P. Autissier, et al. (2006). "CD16+ monocyte-derived macrophages activate resting T cells for HIV infection by producing CCR3 and CCR4 ligands." *J Immunol* 176(10): 5760-71.

Annunziato, F., L. Cosmi, et al. (2007). "Phenotypic and functional features of human Th17 cells." *J Exp Med* 204 (8): 1849-61.

Anderson, R. G. (1998). "The caveolae membrane system." *Annu Rev Biochem* 67: 199-225.

Aoki, T., H. Hagiwara, et al. (2007). "Internalization of caveolae and their relationship with endosomes in cultured human and mouse endothelial cells." *Anat Sci Int* 82(2): 82-97.

Bavari, S., C. M. Bosio, et al. (2002). "Lipid raft microdomains: a gateway for compartmentalized trafficking of Ebola and Marburg viruses." *J Exp Med* 195(5): 593-602.

Benarroch, E. E. (2007). "Lipid rafts, protein scaffolds, and neurologic disease."*Neurology* 69(16): 1635-9.

Berman, N. E., J. K. Marcario, et al. (1999). "Microglial activation and neurological symptoms in the SIV model of NeuroAIDS: association of MHC-II and MMP-9 expression with behavioral deficits and evoked potential changes." *Neurobiol Dis* 6(6): 486-98.

Berta, A. I., A. L. Kiss, et al. (2007). "Different caveolin isoforms in the retina of melanoma malignum affected human eye." *Mol Vis* 13: 881-6.

Berta, A. I., A. L. Kiss, et al. (2007). "Distribution of caveolin isoforms in the lemur retina." *J Vet Sci* 8(3): 295-7.

Bettelli, E., T. Korn, et al. (2007). "Th17: the third member of the effector T cell trilogy."*Curr Opin Immunol* 19(6): 652-7.

Botos, E., A. Turi, et al. (2007). "Regulatory role of kinases and phosphatases on the internalisation of caveolae in HepG2 cells." *Micron* 38(3): 313-20.

Bromberg, J. (2002). "Stat proteins and oncogenesis." *J Clin Invest* 109(9): 1139-42.

Bromberg, J. F. (2001). "Activation of STAT proteins and growth control." *Bioessays* 23(2): 161-9.

Bromley, S. K., A. Iaboni, et al. (2001). "The immunological synapse and CD28-CD80 interactions." *Nat Immunol* 2(12): 1159-66.

Buttner, A., P. Mehraein, et al. (1996). "Vascular changes in the cerebral cortex in HIV-1 infection. II. An immunohistochemical and lectinhistochemical investigation." *Acta Neuropathol* 92(1): 35-41.

Cai, C. and J. Chen (2004). "Overexpression of caveolin-1 induces alteration of multidrug resistance in Hs578T breast adenocarcinoma cells." *Int J Cancer* 111(4): 522-9.

Campbell, S., K. Gaus, et al. (2004). "The raft-promoting property of virion-associated cholesterol, but not the presence of virion-associated Brij 98 rafts, is a determinant of human immunodeficiency virus type 1 infectivity." *J Virol* 78(19): 10556-65.

Campbell, S. M., S. M. Crowe, et al. (2001). "Lipid rafts and HIV-1: from viral entry to assembly of progeny virions." *J Clin Virol* 22(3): 217-27.

Cantin, C., J. Holguera, et al. (2007). "Newcastle disease virus may enter cells by caveolae-mediated endocytosis." *J Gen Virol* 88(Pt 2): 559-69.

Capozza, F., T. M. Williams, et al. (2003). "Absence of caveolin-1 sensitizes mouse skin to carcinogen-induced epidermal hyperplasia and tumor formation." *Am J Pathol* 162 (6): 2029-39.

Chaudhuri, A., F. Duan, et al. (2008). "HIV-1 activates proinflammatory and interferon-inducible genes in human brain microvascular endothelial cells: putative mechanisms of blood-brain barrier dysfunction." *J Cereb Blood Flow Metab* 28(4): 697-711.

Chen, Z. L. and S. Strickland (1997). "Neuronal death in the hippocampus is promoted by plasmin-catalyzed degradation of laminin." *Cell* 91(7): 917-25.

Chen, L., S. Xiong, et al. (2007). "Iron causes interactions of TAK1, p21ras, and phosphatidylinositol 3-kinase in caveolae to activate IkappaB kinase in hepatic macrophages." *J Biol Chem* 282(8): 5582-8.

Cinque, P., A. Bestetti, et al. (2005). "Cerebrospinal fluid interferon-gamma-inducible protein 10 (IP-10, CXCL10) in HIV-1 infection." *J Neuroimmunol* 168(1-2): 154-63.

Clay, C. C., D. S. Rodrigues, et al. (2007). "Neuroinvasion of fluorescein-positive monocytes in acute simian immunodeficiency virus infection." *J Virol* 81(21): 12040-8.

Cohen, A. W., T. P. Combs, et al. (2003). "Role of caveolin and caveolae in insulin signaling and diabetes." *Am J Physiol Endocrinol Metab* 285(6): E1151-60.

Cohen, A. W., R. Hnasko, et al. (2004). "Role of caveolae and caveolins in health and disease." *Physiol Rev* 84(4): 1341-79.

Cohen, A. W., D. S. Park, et al. (2003). "Caveolin-1 null mice develop cardiac hypertrophy with hyperactivation of p42/44 MAP kinase in cardiac fibroblasts." *Am J Physiol Cell Physiol* 284(2): C457-74.

Conant, K., J. C. McArthur, et al. (1999). "Cerebrospinal fluid levels of MMP-2, 7, and 9 are elevated in association with human immunodeficiency virus dementia." *Ann Neurol* 46(3): 391-8.

Couet, J., S. Li, et al. (1997). "Identification of peptide and protein ligands for the caveolin-scaffolding domain. Implications for the interaction of caveolin with caveolae-associated proteins." *J Biol Chem* 272(10): 6525-33.

Creery, D., W. Weiss, et al. (2006). "Differential regulation of CXCR4 and CCR5 expression by interleukin (IL)-4 and IL-13 is associated with inhibition of chemotaxis and human immunodeficiency Virus (HIV) type 1 replication but not HIV entry into human monocytes." *Viral Immunol* 19(3): 409-23.

Csoma, E., T. Deli, et al. (2006). "Human herpesvirus 6A decreases the susceptibility of macrophages to R5 variants of human immunodeficiency virus 1: possible role of RANTES and IL-8." *Virus Res* 121(2): 161-8.

Daniel, C., N. A. Sartory, et al. (2008). "Immune modulatory treatment of trinitrobenzene sulfonic acid colitis with calcitriol is associated with a change of a T helper (Th) 1/Th17 to a Th2 and regulatory T cell profile." *J Pharmacol Exp Ther* 324(1): 23-33.

D'Aversa, T. G., E. A. Eugenin, et al. (2007). "CD40-CD40 ligand interactions in human microglia induce CXCL8 (interleukin-8) secretion by a mechanism dependent on activation of ERK1/2 and nuclear translocation of nuclear factor-kappaB (NFkappaB) and activator protein-1 (AP-1) ." *J Neurosci Res*.

del Peso, L., R. Hernandez-Alcoceba, et al. (1997). "Rho proteins induce metastatic properties in vivo." *Oncogene* 15(25): 3047-57.

del Pozo, M. A., N. Balasubramanian, et al. (2005). "Phospho-caveolin-1 mediates integrin-regulated membrane domain internalization." *Nat Cell Biol* 7(9): 901-8.

Dhillon, B., M. V. Badiwala, et al. (2003). "Caveolin: a key target for modulating nitric oxide availability in health and disease." *Mol Cell Biochem* 247(1-2): 101-9.

Dobrowsky, R. T., S. Rouen, et al. (2005). "Altered neurotrophism in diabetic neuropathy: spelunking the caves of peripheral nerve." *J Pharmacol Exp Ther* 313(2): 485-91.

Dong, X. N., Y. Xiao, et al. (2001). "ELNKWA-epitope specific antibodies induced by epitope-vaccine recognize ELDKWA- and other two neutralizing-resistant mutated epitopes on HIV-1 gp41." *Immunol Lett* 75(2): 149-52.

Dustin, M. L. and L. B. Dustin (2001). "The immunological relay race: B cells take antigen by synapse." *Nat Immunol* 2(6): 480-2.

Engelman, J. A., C. C. Wykoff, et al. (1997). "Recombinant expression of caveolin-1 in oncogenically transformed cells abrogates anchorage-independent growth." *J Biol Chem* 272(26): 16374-81.

Engelman, J. A., C. Chu, et al. (1998). "Caveolin-mediated regulation of signaling along the p42/44 MAP kinase cascade in vivo. A role for the caveolin-scaffolding domain." *FEBS Lett* 428(3): 205-11.

Fantini, J. (2007). "Interaction of proteins with lipid rafts through glycolipid-binding domains: biochemical background and potential therapeutic applications." *Curr Med Chem* 14(27): 2911-7.

Fernandez, I., Y. Ying, et al. (2002). "Mechanism of caveolin filament assembly." *Proc Natl Acad Sci USA* 99(17): 11193-8.

Fernandez, M. A., C. Albor, et al. (2006). "Caveolin-1 is essential for liver regeneration."*Science* 313(5793): 1628-32.

Fine, S. W., M. P. Lisanti, et al. (2005). "Caveolin-3 is a sensitive and specific marker for rhabdomyosarcoma." *Appl Immunohistochem Mol Morphol* 13(3): 231-6.

Fiorucci, G., E. Olivetta, et al. (2007). "Microarray analysis reveals CCL24/eotaxin-2 as an effector of the pathogenetic effects induced by HIV-1 Nef." *Curr Drug Discov Technol* 4(1): 12-23.

Fiucci, G., D. Ravid, et al. (2002). "Caveolin-1 inhibits anchorage-independent growth, anoikis and invasiveness in MCF-7 human breast cancer cells." *Oncogene* 21(15): 2365-75.

Frank, P. G., M. W. Cheung, et al. (2006). "Caveolin-1 and regulation of cellular cholesterol homeostasis." *Am J Physiol Heart Circ Physiol* 291(2): H677-86.

Frank, P. G., G. S. Hassan, et al. (2007). "Caveolae and caveolin-1: novel potential targets for the treatment of cardiovascular disease." *Curr Pharm Des* 13(17): 1761-9.

Frank, P. G. and M. P. Lisanti (2004). "Caveolin-1 and caveolae in atherosclerosis: differential roles in fatty streak formation and neointimal hyperplasia." *Curr Opin Lipidol* 15(5): 523-9.

Frank, P. G. and M. P. Lisanti (2007). "Caveolin-1 and liver regeneration: role in proliferation and lipogenesis." *Cell Cycle* 6(2): 115-6.

Fujimoto, T., H. Kogo, et al. (2001). "Caveolin-2 is targeted to lipid droplets, a new "membrane domain" in the cell." *J Cell Biol* 152(5): 1079-85.

Fujinaga, Y., A. A. Wolf, et al. (2003). "Gangliosides that associate with lipid rafts mediate transport of cholera and related toxins from the plasma membrane to endoplasmic reticulm." *Mol Biol Cell* 14(12): 4783-93.

Galvez, B. G., S. Matias-Roman, et al. (2004). "Caveolae are a novel pathway for membrane-type 1 matrix metalloproteinase traffic in human endothelial cells." *Mol Biol Cell* 15(2): 678-87.

Ghorpade, A., R. Persidskaia, et al. (2001). "Mononuclear phagocyte differentiation, activation, and viral infection regulate matrix metalloproteinase expression: implications for human immunodeficiency virus type 1-associated dementia." *J Virol* 75(14): 6572-83.

Gordon, S. B., E. R. Jarman, et al. (2005). "Reduced interleukin-8 response to *Streptococcus pneumoniae* by alveolar macrophages from adults with HIV/AIDS." *Aids* 19(11): 1197-200.

Gupta, S., R. Boppana, et al. (2008). "Interleukin-12 is necessary for the priming of CD4(+) T cells required during the elicitation of HIV-1 gp120-specific cytotoxic T-lymphocyte function." *Immunology*.

Hall, M. D., R. C. Dolman, et al. (2004). "Platinum(IV) anticancer complexes." *Met Ions Biol Syst* 42: 297-322.

Hanna, Z., E. Priceputu, et al. (2006). "HIV-1 Nef mutations abrogating downregulation of CD4 affect other Nef functions and show reduced pathogenicity in transgenic mice." *Virology* 346(1): 40-52.

Harada, S., R. M. Smith, et al. (1999). "Mechanisms of nuclear translocation of insulin."*Cell Biochem Biophys* 31(3): 307-19.

Harris, J., D. Werling, et al. (2002). "Caveolae and caveolin in immune cells: distribution and functions." *Trends Immunol* 23(3): 158-64.

Harris, T. J., J. F. Grosso, et al. (2007). "Cutting edge: An in vivo requirement for STAT3 signaling in TH17 development and TH17-dependent autoimmunity." *J Immunol* 179 (7): 4313-7.

Herbein, G., A. Varin, et al. (2008). "Nef and TNFalpha are coplayers that favor HIV-1 replication in monocytic cells and primary macrophages." *Curr HIV Res* 6(2): 117-29.

Hess, C., M. Altfeld, et al. (2004). "HIV-1 specific CD8+ T cells with an effector phenotype and control of viral replication." *Lancet* 363(9412): 863-6.

Hirata, T., Y. Osuga, et al. (2007). "Interleukin (IL)-17A stimulates IL-8 secretion, COX2 expression, and cell proliferation of endometriotic stromal cells." *Endocrinology*.

Hofstetter, H. H., A. Kovalovsky, et al. (2007). "Neonatal induction of myelin-specific Th1/Th17 immunity does not result in experimental autoimmune encephalomyelitis and can protect against the disease in adulthood." *J Neuroimmunol* 187(1-2): 20-30.

Hovanessian, A. G., J. P. Briand, et al. (2004). "The caveolin-1 binding domain of HIV-1 glycoprotein gp41 is an efficient B cell epitope vaccine candidate against virus infection." *Immunity* 21(5): 617-27.

Huang, M. C., S. R. Watson, et al. (2007). "Th17 augmentation in OTII TCR plus T cell-selective type 1 sphingosine 1-phosphate receptor double transgenic mice." *J Immunol* 178(11): 6806-13.

Hurtado, P. A., S. Vora, et al. (2008). "Lysyl oxidase propeptide inhibits smooth muscle cell signaling and proliferation." *Biochem Biophys Res Commun* 366(1): 156-61.

Ichinose, K., E. Kawasaki, et al. (2007). "Recent advancement of understanding pathogenesis of type 1 diabetes and potential relevance to diabetic nephropathy." *Am J Nephrol* 27(6): 554-64.

Ikezu, T., H. Ueda, et al. (1998). "Affinity-purification and characterization of caveolins from the brain: differential expression of caveolin-1, -2, and -3 in brain endothelial and astroglial cell types." *Brain Res* 804(2): 177-92.

Ikonen, E., S. Heino, et al. (2004). "Caveolins and membrane cholesterol." *Biochem Soc Trans* 32(Pt 1): 121-3.

Ishikawa, Y., K. Otsu, et al. (2005). "Caveolin; different roles for insulin signal?" *Cell Signal* 17(10): 1175-82.

Isshiki, M., Y. S. Ying, et al. (2002). "A molecular sensor detects signal transduction from caveolae in living cells." *J Biol Chem* 277(45): 43389-98.

Iyengar, P., V. Espina, et al. (2005). "Adipocyte-derived collagen VI affects early mammary tumor progression in vivo, demonstrating a critical interaction in the tumor/stroma microenvironment." *J Clin Invest* 115(5): 1163-76.

Jasmin, J. F., I. Mercier, et al. (2006). "Short-term administration of a cell-permeable caveolin-1 peptide prevents the development of monocrotaline-induced pulmonary hypertension and right ventricular hypertrophy." *Circulation* 114 (9): 912-20.

Johnston, J. B., K. Zhang, et al. (2001). "HIV-1 Tat neurotoxicity is prevented by matrix metalloproteinase inhibitors." *Ann Neurol* 49(2): 230-41.

Jong, A., C. H. Wu, et al. (2008). "Involvement of human CD44 during *Cryptococcus neoformans* infection of brain microvascular endothelial cells." *Cell Microbiol* 10(6): 1313-26.

Jury, E. C., F. Flores-Borja, et al. (2007). "Lipid rafts in T cell signalling and disease."*Semin Cell Dev Biol* 18(5): 608-15.

Kabayama, K., T. Sato, et al. (2007). "Dissociation of the insulin receptor and caveolin-1 complex by ganglioside GM3 in the state of insulin resistance." *Proc Natl Acad Sci USA* 104(34): 13678-83.

Kebir, H., K. Kreymborg, et al. (2007). "Human TH17 lymphocytes promote blood-brain barrier disruption and central nervous system inflammation." *Nat Med* 13(10): 1173-5.

Kelland, L. R., C. F. Barnard, et al. (1994). "A novel trans-platinum coordination complex possessing in vitro and in vivo antitumor activity." *Cancer Res* 54(21): 5618-22.

Kelland, L. R., S. Y. Sharp, et al. (1999). "Mini-review: discovery and development of platinum complexes designed to circumvent cisplatin resistance." *J Inorg Biochem* 77(1-2): 111-5.

Khan, E. M., J. M. Heidinger, et al. (2006). "Epidermal growth factor receptor exposed to oxidative stress undergoes Src- and caveolin-1-dependent perinuclear trafficking." *J Biol Chem* 281(20): 14486-93.

Khan, S., M. S. Bijker, et al. (2007). "Distinct uptake mechanisms but similar intracellular processing of two different toll-like receptor ligand-peptide conjugates in dendritic cells." *J Biol Chem* 282(29): 21145-59.

Ko, Y. G., J. S. Lee, et al. (1999). "TNF-alpha-mediated apoptosis is initiated in caveolae-like domains." *J Immunol* 162(12): 7217-23.

Komers, R., W. E. Schutzer, et al. (2006). "Altered endothelial nitric oxide synthase targeting and conformation and caveolin-1 expression in the diabetic kidney." *Diabetes* 55(6): 1651-9.

Kortylewski, M., M. Kujawski, et al. (2005). "Inhibiting Stat3 signaling in the hematopoietic system elicits multicomponent antitumor immunity." *Nat Med* 11(12): 1314-21.

Koyanagi, Y., W. A. O'Brien, et al. (1988). "Cytokines alter production of HIV-1 from primary mononuclear phagocytes." *Science* 241(4873): 1673-5.

Kumar, A., S. Dhawan, et al. (1999). "Human immunodeficiency virus-1-tat induces matrix metalloproteinase-9 in monocytes through protein tyrosine phosphatase-mediated activation of nuclear transcription factor NF-kappaB." *FEBS Lett* 462(1-2): 140-4.

Landonio, G., A. Sartore-Bianchi, et al. (2001). "Controversies in the management of brain metastases: the role of chemotherapy." *Forum* (Genova) 11(1): 59-74.

Lane, B. R., S. R. King, et al. (2003). "The C—X—C chemokine IP-10 stimulates HIV-1 replication." *Virology* 307(1): 122-34.

Langlet, C., A. M. Bernard, et al. (2000). "Membrane rafts and signaling by the multichain immune recognition receptors." *Curr Opin Immunol* 12(3): 250-5.

Lavie, Y., G. Fiucci, et al. (2001). "Upregulation of caveolin in multidrug resistant cancer cells: functional implications." *Adv Drug Deliv Rev* 49(3): 317-23.

Lee, H., D. S. Park, et al. (2002). "Caveolin-1 mutations (P132L and null) and the pathogenesis of breast cancer: caveolin-1 (P132L) behaves in a dominant-negative manner and caveolin-1 (−/−) null mice show mammary epithelial cell hyperplasia." *Am J Pathol* 161(4): 1357-69.

Li, J., A. Scherl, et al. (2005). "Impaired phagocytosis in caveolin-1 deficient macrophages." *Cell Cycle* 4(11): 1599-607.

Lin, M. I., J. Yu, et al. (2007). "Caveolin-1-deficient mice have increased tumor microvascular permeability, angiogenesis, and growth." *Cancer Res* 67(6): 2849-56.

Lin, M., M. M. DiVito, et al. (2005). "Regulation of pancreatic cancer cell migration and invasion by RhoC GTPase and caveolin-1." *Mol Cancer* 4(1): 21.

Liu, P., M. Rudick, et al. (2002). "Multiple functions of caveolin-1." *J Biol Chem* 277(44): 41295-8.

Llano, M., T. Kelly, et al. (2002). "Blockade of human immunodeficiency virus type 1 expression by caveolin-1."*J Virol* 76(18): 9152-64.

Lombardi, S., C. Garzelli, et al. (1994). "A neutralizing antibody-inducing peptide of the V3 domain of feline immunodeficiency virus envelope glycoprotein does not induce protective immunity." *J Virol* 68(12): 8374-9.

Lu, Y. E. and M. Kielian (2000). "Semliki forest virus budding: assay, mechanisms, and cholesterol requirement." *J Virol* 74(17): 7708-19.

Maek, A. N. W., S. Buranapraditkun, et al. (2007). "Increased interleukin-17 production both in helper T cell subset Th17 and CD4-negative T cells in human immunodeficiency virus infection." *Viral Immunol* 20(1): 66-75.

Mangini, A. J., R. Lafyatis, et al. (2007). "Type I interferons inhibition of inflammatory T helper cell responses in systemic lupus erythematosus." *Ann N Y Acad Sci* 1108: 11-23.

Manie, S, N., S. Debreyne, et al. (2000). "Measles virus structural components are enriched into lipid raft microdomains: a potential cellular location for virus assembly." *J Virol* 74(1): 305-11.

Marsh, M. and A. Pelchen-Matthews (2000). "Endocytosis in viral replication." *Traffic* 1(7): 525-32.

Matko, J. and J. Szollosi (2002). "Landing of immune receptors and signal proteins on lipid rafts: a safe way to be spatio-temporally coordinated?" *Immunol Lett* 82(1-2): 3-15.

Matsukawa, A., S. Kudo, et al. (2005). "Stat3 in resident macrophages as a repressor protein of inflammatory response." *J Immunol* 175(5): 3354-9.

Matteucci, D., P. Mazzetti, et al. (1995). "The feline lymphoid cell line MBM and its use for feline immunodeficiency virus isolation and quantitation." *Vet Immunol Immunopathol* 46(1-2): 71-82.

Mayoral, R., A. Fernandez-Martinez, et al. (2007). "Dispensability and dynamics of caveolin-1 during liver regeneration and in isolated hepatic cells." *Hepatology* 46(3): 813-22.

McMahon, K. A., M. Zhu, et al. (2006). "Detergent-free caveolae proteome suggests an interaction with ER and mitochondria." *Proteomics* 6(1): 143-52.

Medina, F. A., A. W. Cohen, et al. (2007). "Immune dysfunction in caveolin-1 null mice following infection with *Trypanosoma cruzi* (Tulahuen strain)." *Microbes Infect* 9(3): 325-33.

Medina, F. A., C. J. de Almeida, et al. (2006). "Caveolin-1-deficient mice show defects in innate immunity and inflammatory immune response during *Salmonella enterica* serovar Typhimurium infection." *Infect Immun* 74(12): 6665-74.

Medina, F. A., T. M. Williams, et al. (2006). "A novel role for caveolin-1 in B lymphocyte function and the development of thymus-independent immune responses." *Cell Cycle* 5(16): 1865-71.

Michel, V. and M. Bakovic (2007). "Lipid rafts in health and disease." *Biol Cell* 99(3): 129-40.

Mueller, D. L. and M. K. Jenkins (1995). "Molecular mechanisms underlying functional T-cell unresponsiveness." *Curr Opin Immunol* 7(3): 375-81.

Mora, R. C., V. L. Bonilha, et al. (2006). "Bipolar assembly of caveolae in retinal pigment epithelium." *Am J Physiol Cell Physiol* 290(3): C832-43.

Nakamura, S., M. Suzuki, et al. (2007). "IL-2-independent generation of FOXP3(+)CD4(+)CD8(+)CD25(+) cytotoxic regulatory T cell lines from human umbilical cord blood." *Exp Hematol* 35(2): 287-96.

Nguyen, D. H. and J. E. Hildreth (2000). "Evidence for budding of human immunodeficiency virus type 1 selectively from glycolipid-enriched membrane lipid rafts." *J Virol* 74(7): 3264-72.

Nicastri, E., L. Palmisano, et al. (2008). "HIV-1 residual viremia and proviral DNA in patients with suppressed plasma viral load (<400 HIV-RNA cp/ml) during different antiretroviral regimens." *Curr HIV Res* 6(3): 261-6.

Norman, A. W. (2006). "Minireview: vitamin D receptor: new assignments for an already busy receptor." *Endocrinology* 147(12): 5542-8.

Oh, Y. S., K. A. Cho, et al. (2006). "Regulation of insulin response in skeletal muscle cell by caveolin status." *J Cell Biochem* 99(3): 747-58.

Ohnuma, K., M. Uchiyama, et al. (2007). "Caveolin-1 triggers T-cell activation via CD26 in association with CARMA1." *J Biol Chem* 282(13): 10117-31.

Ohnuma, K., T. Yamochi, et al. (2004). "CD26 up-regulates expression of CD86 on antigen-presenting cells by means of caveolin-1." *Proc Natl Acad Sci USA* 101(39): 14186-91.

Okamoto, C. T. (1998). "Endocytosis and transcytosis." *Adv Drug Deliv Rev* 29(3): 215-228.

Olivetta, E., Z. Percario, et al. (2003). "HIV-1 Nef induces the release of inflammatory factors from human monocyte/macrophages: involvement of Nef endocytotic signals and NF-kappa B activation." *J Immunol* 170(4): 1716-27.

Ono, A., S. D. Ablan, et al. (2004). "Phosphatidylinositol (4,5) bisphosphate regulates HIV-1 Gag targeting to the plasma membrane." *Proc Natl Acad Sci USA* 101(41): 14889-94.

Ortegren, U., N. Aboulaich, et al. (2007). "A new role for caveolae as metabolic platforms." *Trends Endocrinol Metab* 18(9): 344-9.

Ouyang, M., S. Lu, et al. (2008). "Visualization of Polarized MT1-MMP activity in live cells by FRET Imaging." *J Biol. Chem.*

Papasavvas, E., J. Sun, et al. (2005). "IL-13 acutely augments HIV-specific and recall responses from HIV-1-infected subjects in vitro by modulating monocytes." *J Immunol* 175(8): 5532-40.

Park, J. M., A. Kim, et al. (2007). "Methylseleninic acid inhibits PMA-stimulated pro-MMP-2 activation mediated by MT1-MMP expression and further tumor invasion through suppression of NF-kappaB activation." *Carcinogenesis* 28(4): 837-47.

Park, S. S., J. E. Kim, et al. (2005). "Caveolin-1 is down-regulated and inversely correlated with HER2 and EGFR expression status in invasive ductal carcinoma of the breast." *Histopathology* 47(6): 625-30.

Parolini, I., M. Sargiacomo, et al. (1999). "Expression of caveolin-1 is required for the transport of caveolin-2 to the plasma membrane. Retention of caveolin-2 at the level of the golgi complex." *J Biol Chem* 274(36): 25718-25.

Parolini, I., S. Topa, et al. (1999). "Phorbol ester-induced disruption of the CD4-Lck complex occurs within a detergent-resistant microdomain of the plasma membrane. Involvement of the translocation of activated protein kinase C isoforms." *J Biol Chem* 274(20): 14176-87.

Patra, S. K. (2007). "Dissecting lipid raft facilitated cell signaling pathways in cancer." *Biochim Biophys Acta*.

Persidsky, Y., M. Stins, et al. (1997). "A model for monocyte migration through the blood-brain barrier during HIV-1 encephalitis." *J Immunol* 158(7): 3499-510.

Pirhonen, J., J. Siren, et al. (2007). "IFN-alpha regulates Toll-like receptor-mediated IL-27 gene expression in human macrophages." *J Leukoc Biol* 82(5): 1185-92.

Pistello, M., F. Bonci, et al. (2005). "Evaluation of feline immunodeficiency virus ORF-A mutants as candidate attenuated vaccine." *Virology* 332(2): 676-90.

Podar, K. and K. C. Anderson (2006). "Caveolin-1 as a potential new therapeutic target in multiple myeloma." *Cancer Lett* 233(1): 10-5.

Power, C., P. A. Kong, et al. (1993). "Cerebral white matter changes in acquired immunodeficiency syndrome dementia: alterations of the blood-brain barrier." *Ann Neurol* 34(3): 339-50.

Puyraimond, A., R. Fridman, et al. (2001). "MMP-2 colocalizes with caveolae on the surface of endothelial cells." *Exp Cell Res* 262(1): 28-36.

Reddy, M. A., S. L. Li, et al. (2006). "Key role of Src kinase in S100B-induced activation of the receptor for advanced glycation end products in vascular smooth muscle cells." *J Biol Chem* 281(19): 13685-93.

Resh, M. D. (1998). "Fyn, a Src family tyrosine kinase." *Int J Biochem Cell Biol* 30(11): 1159-62.

Rey-Cuille, M. A., J. Svab, et al. (2006). "HIV-1 neutralizing antibodies elicited by the candidate CBD1 epitope vaccine react with the conserved caveolin-1 binding motif of viral glycoprotein gp41." *J Pharm Pharmacol* 58(6): 759-67.

Rosenberg, B., L. Vancamp, et al. (1965). "Inhibition of Cell Division in *Escherichia Coli* by Electrolysis Products from a Platinum Electrode." *Nature* 205: 698-9.

Russelakis-Carneiro, M., C. Hetz, et al. (2004). "Prion replication alters the distribution of synaptophysin and caveolin 1 in neuronal lipid rafts." *Am J Pathol* 165(5): 1839-48.

Saez, R., P. Echaniz, et al. (2007). "The impaired response of NK cells from HIV-infected progressor patients to A-class CpG oligodeoxynucleotides is largely dependent of a decreased production of IL-12." *Immunol Lett* 109(1): 83-90.

Santibanez, J. F., F. J. Blanco, et al. (2008). "Caveolin-1 interacts and cooperates with the transforming growth factor-beta type I receptor ALK1 in endothelial caveolae." *Cardiovasc Res* 77(4): 791-9.

Savage, K., S. Leung, et al. (2007). "Distribution and significance of caveolin 2 expression in normal breast and invasive breast cancer: an immunofluorescence and immunohistochemical analysis." *Breast Cancer Res Treat*.

Sawada, N., Y. Taketani, et al. (2007). "Caveolin-1 in extracellular matrix vesicles secreted from osteoblasts." *Bone* 41(1): 52-8.

Sehgal, P. B., G. G. Guo, et al. (2002). "Cytokine signaling: STATS in plasma membrane rafts." *J Biol Chem* 277(14): 12067-74.

Sevigny, J. J., S. M. Albert, et al. (2007). "An evaluation of neurocognitive status and markers of immune activation as predictors of time to death in advanced HIV infection." *Arch Neurol* 64(1): 97-102.

Sexton, P. M., G. Christopoulos, et al. (2008). "Procalcitonin has bioactivity at calcitonin receptor family complexes: potential mediator implications in sepsis." *Crit. Care Med* 36(5): 1637-40.

Shin, J. S, and S, N. Abraham (2001). "Caveolae as portals of entry for microbes."*Microbes Infect* 3(9): 755-61.

Shin, J. S, and S, N. Abraham (2001). "Cell biology. Caveolae—not just craters in the cellular landscape." *Science* 293(5534): 1447-8.

Shin, J. S, and S, N. Abraham (2001). "Co-option of endocytic functions of cellular caveolae by pathogens." *Immunology* 102(1): 2-7.

Sigal, L. H. (2004). "Molecular Biology and Immunology for Clinicians 29: Lipid Domains, Lipid Rafts, and Caveolae." *J Clin Rheumatol* 10(3): 143-146.

Silva, W. I., H. M. Maldonado, et al. (2007). "Caveolins in glial cell model systems: from detection to significance."*J Neurochem* 103 Suppl 1: 101-12.

Simons, K. and E. Ikonen (1997). "Functional rafts in cell membranes." *Nature* 387(6633): 569-72.

Simons, K. and G. van Meer (1988). "Lipid sorting in epithelial cells." *Biochemistry* 27(17): 6197-202.

Singh, G. and J. Koropatnick (1988). "Differential toxicity of cis and trans isomers of dichlorodiammineplatinum." *J Biochem Toxicol* 3: 223-33.

Smart, E. J., G. A. Graf, et al. (1999). "Caveolins, liquid-ordered domains, and signal transduction." *Mol Cell Biol* 19(11): 7289-304.

Solomon, K. R., L. D. Adolphson, et al. (2000). "Caveolae in human and murine osteoblasts." *J Bone Miner Res* 15(12): 2391-401.

Storch, C. H., R. Ehehalt, et al. (2007). "Localization of the human breast cancer resistance protein (BCRP/ABCG2) in lipid rafts/caveolae and modulation of its activity by cholesterol in vitro." *J Pharmacol Exp Ther* 323(1): 257-64.

Straub, A. C., D. B. Stolz, et al. (2007). "Low level arsenic promotes progressive inflammatory angiogenesis and liver blood vessel remodeling in mice." *Toxicol Appl Pharmacol* 222(3): 327-36.

Sui, Z., L. F. Sniderhan, et al. (2007). "Functional synergy between CD40 ligand and HIV-1 Tat contributes to inflammation: implications in HIV type 1 dementia." *J Immunol* 178(5): 3226-36.

Talbott, R. L., E. E. Sparger, et al. (1989). "Nucleotide sequence and genomic organization of feline immunodeficiency virus." *Proc Natl Acad Sci USA* 86(15): 5743-7.

Tamaskar, I. and M. Zhou (2008). "Clinical implications of caveolins in malignancy and their potential as therapeutic targets." *Curr Oncol Rep* 10(2): 101-6.

Taylor, D. R. and N. M. Hooper (2006). "The prion protein and lipid rafts." *Mol Membr Biol* 23(1): 89-99.

Toh, M. L. and P. Miossec (2007). "The role of T cells in rheumatoid arthritis: new subsets and new targets." *Curr Opin Rheumatol* 19(3): 284-8.

Townsend, D. M. and M. H. Hanigan (2002). "Inhibition of gamma-glutamyl transpeptidase or cysteine S-conjugate beta-lyase activity blocks the nephrotoxicity of cisplatin in mice." *J Pharmacol Exp Ther* 300(1): 142-8.

Turkson, J., S. Zhang, et al. (2004). "Inhibition of constitutive signal transducer and activator of transcription 3 activation by novel platinum complexes with potent antitumor activity." *Mol Cancer Ther* 3(12): 1533-42.

Tsuji-Takayama, K., M. Suzuki, et al. (2007). "IL-2 activation of STAT5 enhances production of IL-10 from human cytotoxic regulatory T cells, HOZOT." *Exp Hematol.*

Tzartos, J. S., M. A. Friese, et al. (2007). "Interleukin-17 Production in Central Nervous System-Infiltrating T Cells and Glial Cells Is Associated with Active Disease in Multiple Sclerosis." *Am J Pathol.* van Rossum, D., S. Hilbert, et al. (2008). "Myelin-phagocytosing macrophages in isolated sciatic and optic nerves reveal a unique reactive phenotype." *Glia* 56(3): 271-283.

Vargas, L., B. F. Nore, et al. (2002). "Functional interaction of caveolin-1 with Bruton's tyrosine kinase and Bmx." *J Biol Chem* 277(11): 9351-7.

Veldhoen, M. and B. Stockinger (2006). "TGFbeta1, a "Jack of all trades": the link with pro-inflammatory IL-17-producing T cells." *Trends Immunol* 27(8): 358-61.

Wang, W., M. Milani, et al. (2007). "C57BL/6 mice genetically deficient in IL-12/IL-23 and IFN-gamma are susceptible to experimental autoimmune myasthenia gravis, suggesting a pathogenic role of non-Th1 cells." *J Immunol* 178(11): 7072-80.

Wang, X. M., H. P. Kim, et al. (2006). "Caveolin-1 confers antiinflammatory effects in murine macrophages via the MKK3/p38 MAPK pathway." *Am J Respir Cell Mol Biol* 34(4): 434-42.

Weaver, C. T., R. D. Hatton, et al. (2007). "IL-17 family cytokines and the expanding diversity of effector T cell lineages." *Annu Rev Immunol* 25: 821-52.

Webster, N. L. and S. M. Crowe (2006). "Matrix metalloproteinases, their production by monocytes and macrophages and their potential role in HIV-related diseases." *J Leukoc Biol* 80(5): 1052-66.

Werling, D., J. C. Hope, et al. (1999). "Involvement of caveolae in the uptake of respiratory syncytial virus antigen by dendritic cells." *J Leukoc Biol* 66(1): 50-8.

Wiechen, K., L. Diatchenko, et al. (2001). "Caveolin-1 is down-regulated in human ovarian carcinoma and acts as a candidate tumor suppressor gene." *Am J Pathol* 159(5): 1635-43.

Wiechen, K., C. Sers, et al. (2001). "Down-regulation of caveolin-1, a candidate tumor suppressor gene, in sarcomas." *Am J Pathol* 158(3): 833-9.

Wiedermann, F. J., N. Kaneider, et al. (2002). "Migration of human monocytes in response to procalcitonin." *Crit. Care Med* 30(5): 1112-7.

Williams, T. M. and M. P. Lisanti (2004). "The Caveolin genes: from cell biology to medicine." *Ann Med* 36(8): 584-95.

Williams, T. M. and M. P. Lisanti (2004). "The caveolin proteins." *Genome Biol* 5(3): 214.

Williams, T. M. and M. P. Lisanti (2005). "Caveolin-1 in oncogenic transformation, cancer, and metastasis." *Am J Physiol Cell Physiol* 288(3): C494-506.

Williams, T. M., F. Medina, et al. (2004). "Caveolin-1 gene disruption promotes mammary tumorigenesis and dramatically enhances lung metastasis in vivo. Role of Cav-1 in cell invasiveness and matrix metalloproteinase (MMP-2/9) secretion." *J Biol Chem* 279(49): 51630-46.

Wolk, K., E. Witte, et al. (2007). "IL-22 induces lipopolysaccharide-binding protein in hepatocytes: a potential systemic role of IL-22 in Crohn's disease." *J Immunol* 178(9): 5973-81.

Xu, L., A. Kitani, et al. (2007). "Cutting edge: regulatory T cells induce CD4+ CD25-Foxp3-T cells or are self-induced to become Th17 cells in the absence of exogenous TGF-beta." *J Immunol* 178(11): 6725-9.

Yarchoan, R., J. M. Pluda, et al. (2007). "Treatment of AIDS-related Kaposi's sarcoma with interleukin-12: rationale and preliminary evidence of clinical activity." *Crit Rev Immunol* 27(5): 401-14.

Yu, H. and R. Jove (2004). "The STATs of cancer—new molecular targets come of age." *Nat Rev Cancer* 4(2): 97-105.

What is claimed is:

1. A method for reducing matrix metalloproteinases (MMP) in a patient in need thereof, the method comprising administering an effective amount of a platinum(IV) compound effective for reducing the MMP to the patient, the platinum (IV) compound comprising the structure shown in at least one of formula (II) or (IV):

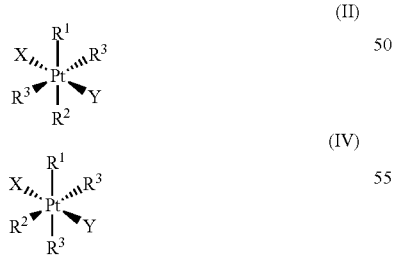

wherein X and Y are, independently, any halogen, —CN, —SCN, —NCS, —$NO_2$, —ONO, —$OHSO_3$, —$OH_2PO_3$, —$OHSO_2$, —$SO_3H$, —OH, —$OR^2$, —OS$(CH_3)_2$, —$OCOR^2$, —$OCOOR^2$, —$OSO_2OH_3$, —SH, —$SR^2$, —$S_2CN(R^2)_2$, —$OSiO_3$, —$OBO_2H$, —$OHSeO_2$, —NHCOH, —$NH_2CHO$, —$NH_2CH_2OH$, —$NH_2C(OH)_3$ or —$NH_2CH(OH)_2$ or —$NHCOR^2$, or X and Y together form a ring structure selected from the group consisting of cyclobutane dicarboxylate (CB-DCA) $(OCOC_4H_6OCO)^{2-}$; oxalate $(O_2O_4)^{2-}$, malanato $(OOCCH_2COO)^{2-}$, dithiocarbamate $((R^2)_2NCS_2)^-$, acetylacetonate $(CH_3COCHCOCH_3)^-$, carboxylate $(CO_2R^2)^-$, sulfate $(SO_4)^2$, phosphate $(HPO_4)^{2-}$, selenate $(SeO_4)^{2-}$, silicate $(SiO_4)^{2-}$, diborate $(B_2O_5)^{4-}$, (acetylacetonate $(OCCH_3CH_2CH_3O)^-$, ethylene diamine $(H_2C_2H_4NH_2)$, bis(diphenylphosphino)ethane (dppe) $((C_6H_5)_2PC_2H_4P(C_6H_5)_2)$, bis(dimethylphosphino)ethane (dmpe) $((CH_3)_2PC_2H_4P(CH_3)_2)$, 2,2'-bipyridine $((NC_5H_4)_2)$ and glyme $(CH_3OCH_2CH_2OCH_3)$;

$R^1$ is —$NO_2$, —ONO, —CN, —SCN, —NCS, —COOH, $COOR^2$, —CHO, —COR or —$SO_3H$;

$R^2$ is an alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with any halogen, —COOH, —OH, —$NO_2$, —$NH_2$, —$HSO_3$, —$HSO_3$, —$OH_2PO_3$, —$OBO_2$, —$OHSiO_3$, —$OHSeO_2$, N-alkyl, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^3$ is —$NH_3$, —$NH_2R^2$, —$NH(R^2)_2$, —$N(R^2)_3$, —$NH_2COR^2$, —$NH_2COH$, —$NH_2CHO$, —$NH_2CH_2OH$, —$NH_2C(OH)_3$, —$NH_2CH(OH)_2$, —$OCH_3$ or —$OR^2$, or $R^3$, $R^3$, X, and Y together comprise porphyrin or phthalocyanine;

or a pharmaceutically acceptable salt thereof.

2. The method of claim 1, wherein X and Y are independently selected from the group consisting of F, Cl, Br, and I; $R^1$ is —$NO_2$; $R^2$ is Cl; and $R^3$ is —$NH_3$.

3. The method of claim 2, wherein X and Y are Cl.

4. A method for reducing matrix metalloproteinases (MMP) in a patient in need thereof, the method comprising administering an effective amount of a platinum(IV) compound effective for reducing MMP to the patient, the platinum(IV) compound comprising the structure shown in at least one of formula (II) or (IV):

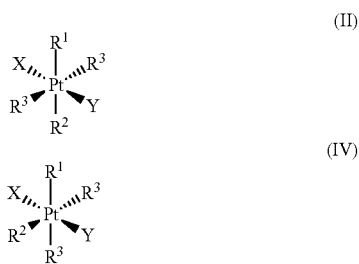

wherein X and Y are, independently, any halogen, —CN, —SCN, —NCS, —$NO_2$, —ONO, —$OHSO_3$, —$OH_2PO_3$, —$OHSO_2$, —$SO_3H$, —OH, —$OR^2$, —OS$(CH_3)_2$, —$OCOR^2$, —$OCOOR^2$, —$OSO_2OH_3$, —SH, —$SR^2$, —$S_2CN(R^2)_2$, —$OSiO_3$, —$OBO_2H$, —$OHSeO_2$, —NHCOH, —$NH_2CHO$, —$NH_2CH_2OH$, —$NH_2C(OH)_3$ or —$NH_2CH(OH)_2$ or —$NHCOR^2$, or X and Y together form a ring structure selected from the group consisting of cyclobutane dicarboxylate (CB-DCA) $(OCOC_4H_6OCO)^{2-}$; oxalate $(O_2O_4)^{2-}$, malanato $(OOCCH_2COO)^{2-}$, dithiocarbamate $((R^2)_2NCS_2)^-$, acetylacetonate $(CH_3COCHCOCH_3)^-$, carboxylate $(CO_2R^2)^-$, sulfate $(SO_4)^2$, phosphate $(HPO_4)^{2-}$, selenate $(SeO_4)^{2-}$, silicate $(SiO_4)^{2-}$, diborate $(B_2O_5)^{4-}$ (acetylacetonate $(OCCH_3CH_2CH_3O)^-$, ethylene diamine $(H_2C_2H_4NH_2)$, bis(diphenylphosphino)ethane (dppe) $((C_6H_5)_2PC_2H_4P(C_6H_5)_2)$, bis(dimethylphosphino)ethane (dmpe) $((CH_3)_2PC_2H_4P(CH_3)_2)$, 2,2'-bipyridine $((NC_5H_4)_2)$ and glyme $(CH_3OCH_2CH_2OCH_3)$;

$R^1$ is —$NO_2$, —ONO, —CN, —SCN, —NCS, —COOH, $COOR^2$, —CHO, —COR or —$SO_3H$;

$R^2$ is chloride, bromide, fluoride or iodide; —COOH, —OH, —$NH_2$, —$HSO_3$, —$OHSO_3$, —$OH_2PO_3$, —$OBO_2$, —$OHSiO_3$, —$OHSeO_2$, folate, N-acetylcysteine, taurine, ethanolamine, safranin, riboflavin, 7-ethoxycoumarin, methylene blue, thiamine, caffeine, N-acetyl galactosamine, naringin, N-acetyl neuraminic acid, methyl alpha-D-mannopyranoside, xanthine, hydantoin, 6-aminonicotinamide, theophylline, N-acetyl glucosamine, alpha-aminoisobutyric acid, cytarabine, pantothenic acid, nicotinamide, fluorescein, rhodamine, biotin, inosine, theobromine, histidine, niacine, eosin, luminol, pyrimidine, thiosalicylic acid, 7-amino-4-methylcoumarin, tris, nicotine, 2,6-dichloro-4-nitropyridine, 2,6-dimethyl-4-nitropyridine, quinoline, pyridoxine, nicotinic acid, carbazole, morpholine, pyrimidinecarboxylic acid, imidazole, thiazole, oxazole, succinimidyl ester, pyridine, benzimidazole, benzoxazole, 2-(2-aminophenyl)-benzothiazole, 2-(4-aminophenyl)-benzothiazole, benzothiazole, hydroorotic acid, palmitate, purine, adenine, guanine, hypoxanthine, uric acid, isoguanine, serine, cytosine, thymidine, uracil, myristic acid, oleic acid, succinimide, triethanolamine, diethanolamine, thiazolidinedione, flavin, anthranilic acid, methionine, cysteine, tyrosine, threonine, N-acetyl mannose;

$R^3$ is —$NH_3$, —$NH_2R^2$, —$NH(R^2)_2$, —$N(R^2)_3$, —$NH_2COR^2$, —$NH_2COH$, —$NH_2CHO$, —$NH_2CH_2OH$, —$NH_2C(OH)_3$, —$NH_2CH(OH)_2$, —$OCH_3$ or —$OR^2$, or $R^3$, $R^3$, X, and Y together comprise porphyrin or phthalocyanine;

or $R^3$, $R^2$, X, and Y together comprise porphyrin or phthalocyanine;

or a pharmaceutically acceptable salt thereof.

5. The method of claim 1, wherein the matrix metalloproteinase is at least one of MT MMP 1, MMP 2, or MMP 9.

6. The method of claim 4, wherein the matrix metalloproteinase is at least one of MT MMP 1, MMP 2, or MMP 9.

7. A method for reducing matrix metalloproteinases (MMP) in a patient in need thereof, the method comprising administering an effective amount of a platinum (IV) compound effective for reducing the MMP to the patient, the platinum (IV) compound comprising the structure shown in at least one of formula (I) or (III):

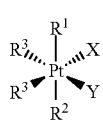

(I)

-continued

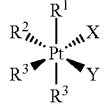

(III)

wherein X and Y are, independently, any halogen, —CN, —SCN, —NCS, —$NO_2$, —ONO, —$OHSO_3$, —$OH_2PO_3$, —$OHSO_2$, —$SO_3H$, —OH, —$OR^2$, —OS$(CH_3)_2$, —$OCOR^2$, —$OCOOR^2$, —$OSO_2OH_3$, —SH, —$SR^2$, —$S_2CN(R^2)_2$, —$OSiO_3$, —$OBO_2H$, —$OHSeO_2$, —NHCOH, —$NH_2CHO$, —$NH_2CH_2OH$, —$NH_2C(OH)_3$ or —$NH_2CH(OH)_2$ or —$NHCOR^2$, or X and Y together form a ring structure selected from the group consisting of cyclobutane dicarboxylate (CB-DCA) $(OCOC_4H_6OCO)^{2-}$; oxalate $(C_2O_4)^{2-}$, malanato $(OOCCH_2COO)^{2-}$, dithiocarbamate $((R^2)_2NCS_2)^-$, acetylacetonate $(CH_3COCHCOCH_3)^-$, carboxylate $(CO_2R^2)^-$, sulfate $(SO_4)^2$, phosphate $(HPO_4)^{2-}$, selenate $(SeO_4)^{2-}$, silicate $(SiO_4)^{2-}$, diborate $(B_2O_5)^{4-}$, (acetylacetonate $(OCCH_3CH_2CH_3O)^-$, ethylene diamine $(H_2C_2H_4NH_2)$, bis(diphenylphosphino)ethane (dppe) $((C_6H_5)_2PC_2H_4P(C_6H_5)_2)$, bis(dimethylphosphino)ethane (dmpe) $((CH_3)_2PC_2H_4P(CH_3)_2)$, 2,2'-bipyridine $((NC_5H_4)_2)$ and glyme $(CH_3OCH_2CH_2OCH_3)$;

$R^1$ is —$NO_2$, —ONO, —CN, —SCN, —NCS, —COOH, $COOR^2$, —CHO, —COR or —$SO_3H$;

$R^2$ is an alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with any halogen, —COOH, —OH, —$NO_2$, —$NH_2$, —$HSO_3$, —$HSO_3$, —$OH_2PO_3$, —$OBO_2$, —$OHSiO_3$, —$OHSeO_2$, N-alkyl, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^3$ is —$NH_3$, —$NH_2R^2$, —$NH(R^2)_2$, —$N(R^2)_3$, —$NH_2COR^2$, —$NH_2COH$, —$NH_2CHO$, —$NH_2CH_2OH$, —$NH_2C(OH)_3$, —$NH_2CH(OH)_2$, —$OCH_3$ or —$OR^2$, or $R^3$, $R^3$, X, and Y together comprise porphyrin or phthalocyanine;

or a pharmaceutically acceptable salt thereof.

8. The method of claim 5, wherein X and Y are independently selected from the group consisting of F, Cl, Br, and I; $R^1$ is —$NO_2$; $R^2$ is Cl; and $R^3$ is —$NH_3$.

9. The method of claim 8, wherein X and Y are Cl.

10. The method of claim 7, wherein the matrix metalloproteinase is at least one of MT MMP 1, MMP 2, or MMP 9.

11. A method for reducing matrix metalloproteinases (MMP) in a patient in need thereof, the method comprising administering an effective amount of a platinum(IV) compound effective for reducing MMP to the patient, the platinum(IV) compound comprising the structure shown in at least one of formula I or III:

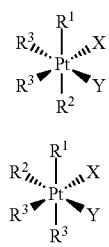

(I)

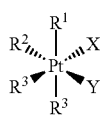

(III)

wherein X and Y are, independently, any halogen, —CN, —SCN, —NCS, —NO$_2$, —ONO, —OHSO$_3$, —OH$_2$PO$_3$, —OHSO$_2$, —SO$_3$H, —OH, —OR$^2$, —OS(CH$_3$)$_2$, —OCOR$^2$, —OCOOR$^2$, —OSO$_2$OH$_3$, —SH, —SR$^2$, —S$_2$CN(R$^2$)$_2$, —OSiO$_3$, —OBO$_2$H, —OHSeO$_2$, —NHCOH, —NH$_2$CHO, —NH$_2$CH$_2$OH, —NH$_2$C(OH)$_3$ or —NH$_2$CH(OH)$_2$ or —NHCOR$^2$, or X and Y together form a ring structure selected from the group consisting of cyclobutane dicarboxylate (CBDCA) (OCOC$_4$H$_6$OCO)$^{2-}$; oxalate (O$_2$O$_4$)$^{2-}$, malanato (OOCCH$_2$COO)$^{2-}$, dithiocarbamate ((R$^2$)$_2$NCS$_2$)$^-$, acetylacetonate (CH$_3$COCHCOCH$_3$)$^-$, carboxylate (CO$_2$R$^2$)$^-$, sulfate (SO$_4$)$^2$, phosphate (HPO$_4$)$^{2-}$, selenate (SeO$_4$)$^{2-}$, silicate (SiO$_4$)$^{2-}$, diborate (B$_2$O$_5$)$^{4-}$, (acetylacetonate (OCCH$_3$CH$_2$CH$_3$O)$^-$, ethylene diamine (H$_2$C$_2$H$_4$NH$_2$), bis(diphenylphosphino)ethane (dppe) ((C$_6$H$_5$)$_2$PC$_2$H$_4$P(C$_6$H$_5$)$_2$), bis(dimethylphosphino)ethane (dmpe) ((CH$_3$)$_2$PC$_2$H$_4$P(CH$_3$)$_2$), 2,2'-bipyridine ((NC$_5$H$_4$)$_2$) and glyme (CH$_3$OCH$_2$CH$_2$OCH$_3$);

R$^1$ is —NO$_2$, —ONO, —CN, —SCN, —NCS, —COOH, COOR$^2$, —CHO, —COR or —SO$_3$H;

R$^2$ is chloride, bromide, fluoride or iodide; —COOH, —OH, —NH$_2$, —HSO$_3$, —OHSO$_3$, —OH$_2$PO$_3$, —OBO$_2$, —OHSiO$_3$, —OHSeO$_2$, folate, N-acetylcysteine, taurine, ethanolamine, safranin, riboflavin, 7-ethoxycoumarin, methylene blue, thiamine, caffeine, N-acetyl galactosamine, naringin, N-acetyl neuraminic acid, methyl alpha-D-mannopyranoside, xanthine, hydantoin, 6-aminonicotinamide, theophylline, N-acetyl glucosamine, alpha-aminoisobutyric acid, cytarabine, pantothenic acid, nicotinamide, fluorescein, rhodamine, biotin, inosine, theobromine, histidine, niacine, eosin, luminol, pyrimidine, thiosalicylic acid, 7-amino-4-methylcoumarin, tris, nicotine, 2,6-dichloro-4-nitropyridine, 2,6-dimethyl-4-nitropyridine, quinoline, pyridoxine, nicotinic acid, carbazole, morpholine, pyrimidinecarboxylic acid, imidazole, thiazole, oxazole, succinimidyl ester, pyridine, benzimidazole, benzoxazole, 2-(2-aminophenyl)-benzothiazole, 2-(4-aminophenyl)-benzothiazole, benzothiazole, hydroorotic acid, palmitate, purine, adenine, guanine, hypoxanthine, uric acid, isoguanine, serine, cytosine, thymidine, uracil, myristic acid, oleic acid, succinimide, triethanolamine, diethanolamine, thiazolidinedione, flavin, anthranilic acid, methionine, cysteine, tyrosine, threonine, N-acetyl mannose;

R$^3$ is —NH$_3$, —NH$_2$R$^2$, —NH(R$^2$)$_2$, —N(R$^2$)$_3$, —NH$_2$COR$^2$, —NH$_2$COH, —NH$_2$CHO, —NH$_2$CH$_2$OH, —NH$_2$C(OH)$_3$, —NH$_2$CH(OH)$_2$, —OCH$_3$ or —OR$^2$, or R$^3$, R$^3$, X, and Y together comprise porphyrin or phthalocyanine;

or R$^3$, R$^2$, X, and Y together comprise porphyrin or phthalocyanine;

or a pharmaceutically acceptable salt thereof.

12. The method of claim 11, wherein the matrix metalloproteinase is at least one of MT MMP 1, MMP 2, or MMP 9.

* * * * *